(12) United States Patent
Horiuchi et al.

(10) Patent No.: US 12,115,011 B2
(45) Date of Patent: Oct. 15, 2024

(54) RADIATION DETECTOR AND RADIOGRAPHY APPARATUS

(71) Applicant: FUJIFILM CORPORATION, Tokyo (JP)

(72) Inventors: Hisatsugu Horiuchi, Kanagawa (JP); Munetaka Kato, Kanagawa (JP); Tatsuya Taneichi, Kanagawa (JP); Naoyuki Nishino, Kanagawa (JP); Takeyasu Kobayashi, Kanagawa (JP)

(73) Assignee: FUJIFILM CORPORATION, Tokyo (JP)

( * ) Notice: Subject to any disclaimer, the term of this patent is extended or adjusted under 35 U.S.C. 154(b) by 262 days.

(21) Appl. No.: 17/807,858

(22) Filed: Jun. 20, 2022

(65) Prior Publication Data

US 2023/0016138 A1    Jan. 19, 2023

(30) Foreign Application Priority Data

Jul. 19, 2021    (JP) .................................. 2021-118903

(51) Int. Cl.
*A61B 6/00* (2024.01)
*A61B 6/03* (2006.01)
(Continued)

(52) U.S. Cl.
CPC ............ *A61B 6/4435* (2013.01); *A61B 6/032* (2013.01); *A61B 6/4085* (2013.01); *G01N 23/046* (2013.01); *G01N 2223/419* (2013.01)

(58) Field of Classification Search
CPC ..... A61B 6/4435; A61B 6/032; A61B 6/4085; A61B 6/0478; A61B 6/4405; A61B 6/04; (Continued)

(56) References Cited

U.S. PATENT DOCUMENTS

| 5,804,832 A * | 9/1998 | Crowell ..................... G01T 1/24 |
| | | 250/580 |
| 6,273,606 B1 * | 8/2001 | Dewaele ............... A61B 6/5241 |
| | | 378/98.12 |

(Continued)

FOREIGN PATENT DOCUMENTS

JP    2003-339688 A    12/2003

*Primary Examiner* — David P Porta
*Assistant Examiner* — Mamadou Faye
(74) *Attorney, Agent, or Firm* — SOLARIS Intellectual Property Group, PLLC

(57) ABSTRACT

A radiation detector includes a sensor panel unit, a support table to which the sensor panel unit is attached, and two fixing members. The sensor panel unit includes two sensor panels. The sensor panel has pixels that sense visible light converted from radiation and generate charge. The sensor panel unit has a configuration in which an end portion of one sensor panel and an end portion of the other sensor panel are arranged to overlap each other in a thickness direction. A first fixing member fixes two sensor panels in an overlap region in which the end portions overlap. A second fixing member fixes the sensor panel unit and the support table in the overlap region. The second fixing member at least partially overlaps the first fixing member in the overlap region in a plan view of the sensor panel unit in the thickness direction.

25 Claims, 28 Drawing Sheets

(51) Int. Cl.
*A61B 6/40* (2024.01)
*G01N 23/046* (2018.01)

(58) Field of Classification Search
CPC .............. A61B 6/4266; G01N 23/046; G01N 2223/419
See application file for complete search history.

(56) References Cited

U.S. PATENT DOCUMENTS

| | | |
|---|---|---|
| 2003/0200655 A1 | 10/2003 | Vafi et al. |
| 2006/0185165 A1 | 8/2006 | Vafi et al. |
| 2008/0054222 A1* | 3/2008 | Sakai .................. C09K 11/628 |
| | | 252/301.4 H |
| 2013/0306877 A1* | 11/2013 | Pohan ................... G01T 1/2985 |
| | | 250/394 |
| 2019/0120977 A1* | 4/2019 | Jacobs ................ G01T 1/20188 |

* cited by examiner

FIG. 19

IRRADIATION CONDITION TABLE 141

| IMAGING PROCEDURE | | | IRRADIATION CONDITIONS 156 | | | |
|---|---|---|---|---|---|---|
| | | | (TUBE VOLTAGE | TUBE CURRENT | IRRADIATION TIME) | |
| STANDING POSTURE | HEAD | ADULT MALE | 100 KV | 10 mA | 0.5 ms | ... |
| STANDING POSTURE | HEAD | ADULT FEMALE | 100 KV | 10 mA | 0.5 ms | ... |
| STANDING POSTURE | NECK | ADULT MALE | 80 KV | 8 mA | 0.5 ms | ... |
| ⋮ | | | ⋮ | | | |
| SITTING POSTURE | SPINE | ADULT MALE | 120 KV | 12 mA | 0.5 ms | ... |
| SITTING POSTURE | SPINE | ADULT FEMALE | 120 KV | 12 mA | 0.5 ms | ... |
| ⋮ | | | ⋮ | | | |

RADIATION DETECTOR AND RADIOGRAPHY APPARATUS

CROSS-REFERENCE TO RELATED APPLICATIONS

The present application claims priority under 35 U.S.C. § 119 to Japanese Patent Application No. 2021-118903, filed on Jul. 19, 2021. The above application is hereby expressly incorporated by reference, in its entirety, into the present application.

BACKGROUND

1. Technical Field

The technology of the present disclosure relates to a radiation detector and a radiography apparatus.

2. Description of the Related Art

A radiation detector is known which detects radiation transmitted through a subject and outputs a radiographic image of the subject. An imaging sensor is provided in the radiation detector. The imaging sensor has pixels. The pixels sense the radiation or visible light converted from the radiation and generate charge. A radiographic image is obtained by reading out the charge from the pixels and performing various types of signal processing.

JP2003-339688A discloses a radiation detector having an imaging sensor unit in which a plurality of imaging sensors having a rectangular plate shape are arranged. FIG. 12 of JP2003-339688A illustrates the imaging sensor unit in which end portions of two adjacent imaging sensors overlap each other in a thickness direction.

SUMMARY

In a case in which end portions of two adjacent imaging sensors overlap each other in a thickness direction as in the aspect illustrated in FIG. 12 of JP2003-339688A, the two imaging sensors are fixed in the overlapped end portions, and the imaging sensor unit is attached to one support table. However, the thermal expansion or contraction of the two imaging sensors differs depending on how to fix the two imaging sensors and how to attach the imaging sensor unit to the support table. As a result, there is a concern that the reproducibility of the positions of the two imaging sensors will be reduced. Specifically, in a case in which the imaging sensor returns to the original state after thermal expansion or contraction, there is a concern that the position of each of the two imaging sensors will deviate from the original position.

One embodiment according to the technology of the present disclosure is to provide a radiation detector and a radiography apparatus that can improve the reproducibility of positions of two imaging sensors in which end portions are arranged to overlap each other.

According to an aspect of the present disclosure, there is provided a radiation detector comprising: an imaging sensor unit which includes at least two imaging sensors of a first imaging sensor and a second imaging sensor that have a rectangular plate shape and include pixels that sense radiation, which has been emitted from a radiation source and transmitted through a subject, or visible light converted from the radiation and generate charge and in which a first end portion of the first imaging sensor and a second end portion of the second imaging sensor are arranged to overlap each other in a thickness direction; a support table to which the imaging sensor unit is attached; a first fixing member that fixes the first imaging sensor and the second imaging sensor in an overlap region in which the first end portion and the second end portion overlap each other; and a second fixing member that fixes the imaging sensor unit and the support table in the overlap region and at least partially overlaps the first fixing member in the overlap region in a plan view of the imaging sensor unit in the thickness direction.

Preferably, the first fixing member partially fixes the first imaging sensor and the second imaging sensor, and the second fixing member partially fixes the imaging sensor unit and the support table.

Preferably, a first imaging region in which the pixels are arranged in the first imaging sensor and a second imaging region in which the pixels are arranged in the second imaging sensor overlap in the overlap region in a plan view of the imaging sensor unit in the thickness direction. Preferably, in a case in which the first imaging sensor is disposed closer to an incident side of the radiation than the second imaging sensor in the thickness direction, the first fixing member is disposed at a position that does not protrude from an overlap imaging region in which the first imaging region and the second imaging region overlap toward the second imaging region.

Preferably, the first fixing member has the same width as the overlap region.

Preferably, the radiation detector further comprises a spacer that is provided between the first imaging sensor and the support table and has a thickness corresponding to a distance between the first imaging sensor and the support table in a case in which the first imaging sensor is disposed closer to an incident side of the radiation than the second imaging sensor in the thickness direction.

Preferably, the radiation detector further comprises a third fixing member that fixes the first imaging sensor and the spacer at a position adjacent to the first fixing member.

Preferably, the imaging sensor unit includes two imaging sensors of the first imaging sensor and the second imaging sensor.

Preferably, the support table has an attachment surface that is convex toward an opposite side of the radiation source, and the imaging sensor unit is attached to the attachment surface following the convex shape.

Preferably, the convex shape is a U-shape or a V-shape.

Preferably, in a case in which the first imaging sensor is disposed closer to an incident side of the radiation than the second imaging sensor in the thickness direction and the convex shape is the U-shape, a tangent line between the first imaging sensor and the first fixing member is parallel to a tangent line between the second imaging sensor and the second fixing member.

Preferably, the imaging sensor is a sensor panel in which the pixels including thin film transistors are two-dimensionally arranged.

Preferably, a substrate of the sensor panel has a thickness that is equal to or less than 100 μm.

Preferably, the support table is made of metal, and a substrate of the sensor panel is made of a resin.

Preferably, the support table has an attachment surface to which a first surface of the imaging sensor is attached, and the radiation detector further comprises a contact member that comes into contact with a second surface of the imaging sensor which is opposite to the first surface.

Preferably, the contact member biases the imaging sensor to the attachment surface.

Preferably, the contact member is deformed according to thermal expansion and contraction of the imaging sensor in a direction parallel to the attachment surface.

Preferably, in the contact member, a first length along a normal direction to the attachment surface is larger than a second length along a direction parallel to the attachment surface.

Preferably, the attachment surface has a convex shape toward an opposite side of the radiation source, and a surface of the contact member which comes into contact with the second surface has a shape following the convex shape.

Preferably, the radiation detector further comprises a holding member that holds the contact member while pressing the contact member against the imaging sensor and has a higher rigidity than the contact member.

Preferably, the second surface has an imaging region in which the pixels are arranged and a non-imaging region which is provided around the imaging region and in which the pixels are not arranged, and the contact member comes into contact with the non-imaging region.

Preferably, a circuit board is attached to a first side of the imaging sensor, and the contact member biases the imaging sensor to the attachment surface and includes a first contact member that is disposed on the first side and a second contact member that is disposed on a second side of the imaging sensor which faces the first side and to which the circuit board is not attached. Preferably, the first contact member has a higher biasing force than the second contact member.

Preferably, a circuit board is attached to the imaging sensor, and a radiation shielding member that shields the radiation to protect the circuit board is attached to the contact member.

According to another aspect of the present disclosure, there is provided a radiography apparatus comprising the above-described radiation detector and the radiation source.

Preferably, the radiography apparatus further comprises: an annular frame to which the radiation detector and the radiation source are attached and in which a subject is positioned in a cavity; and a rotation mechanism that rotates the frame around the subject to capture radiographic images of the subject at different angles. Preferably, the support table has an attachment surface that has an arc surface shape following the annular frame, and the imaging sensor unit is attached to the attachment surface following the arc surface shape.

Preferably, the radiography apparatus is a computed tomography apparatus that obtains a tomographic image of the subject on the basis of the radiographic images captured at different angles.

Preferably, the radiation source emits the radiation having a conical shape.

Preferably, the subject is positioned in the cavity in either a standing posture or a sitting posture.

According to the technology of the present disclosure, it is possible to provide a radiation detector and a radiography apparatus that can improve the reproducibility of the positions of two imaging sensors in which end portions are arranged to overlap each other.

BRIEF DESCRIPTION OF THE DRAWINGS

Exemplary embodiments according to the technique of the present disclosure will be described in detail based on the following figures, wherein:

FIG. 19 is a diagram illustrating an irradiation condition table;

DETAILED DESCRIPTION

First Embodiment

Figure 1:
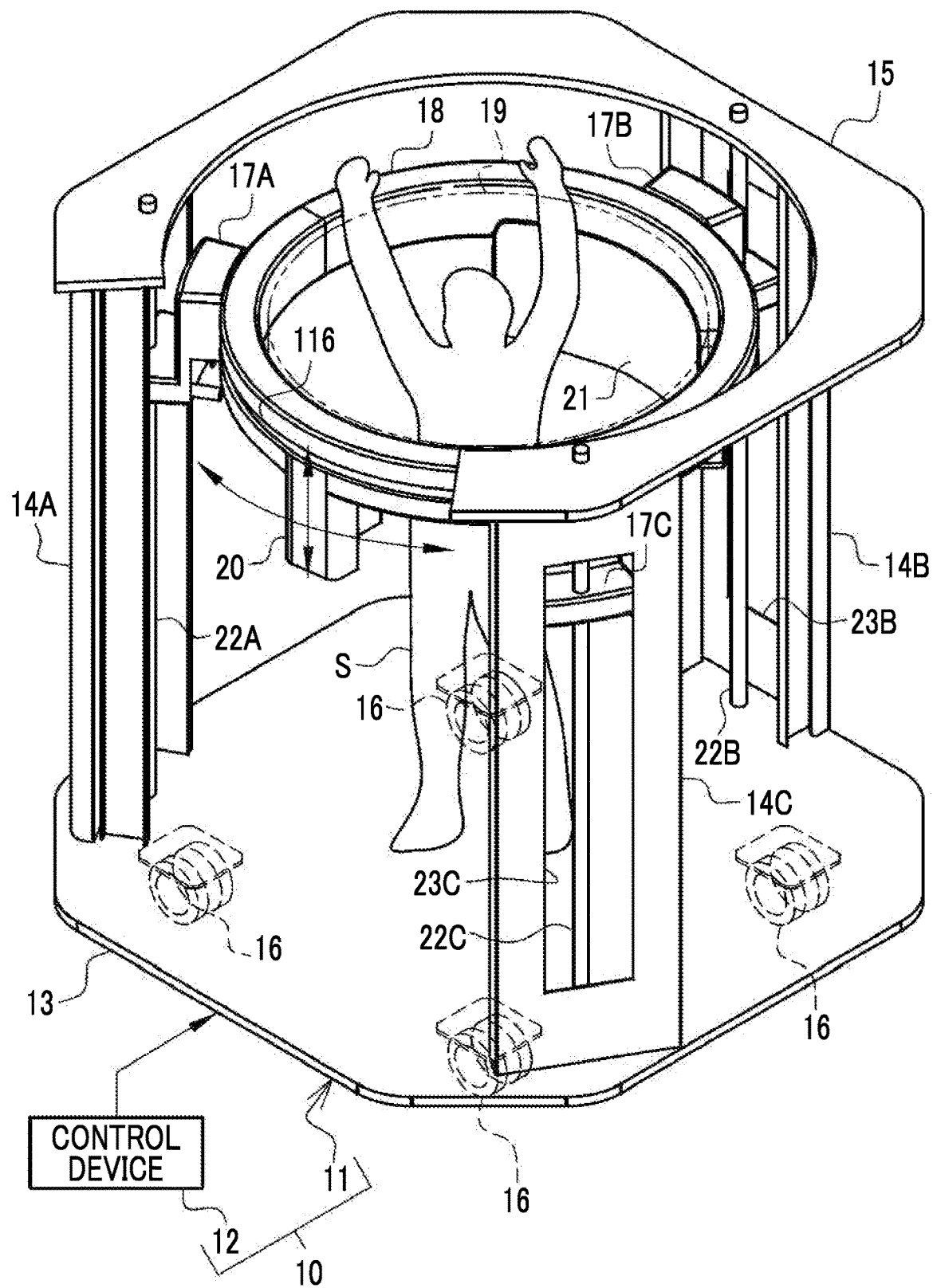
FIG. 1 is a perspective view illustrating a CT apparatus.
Figure 2:
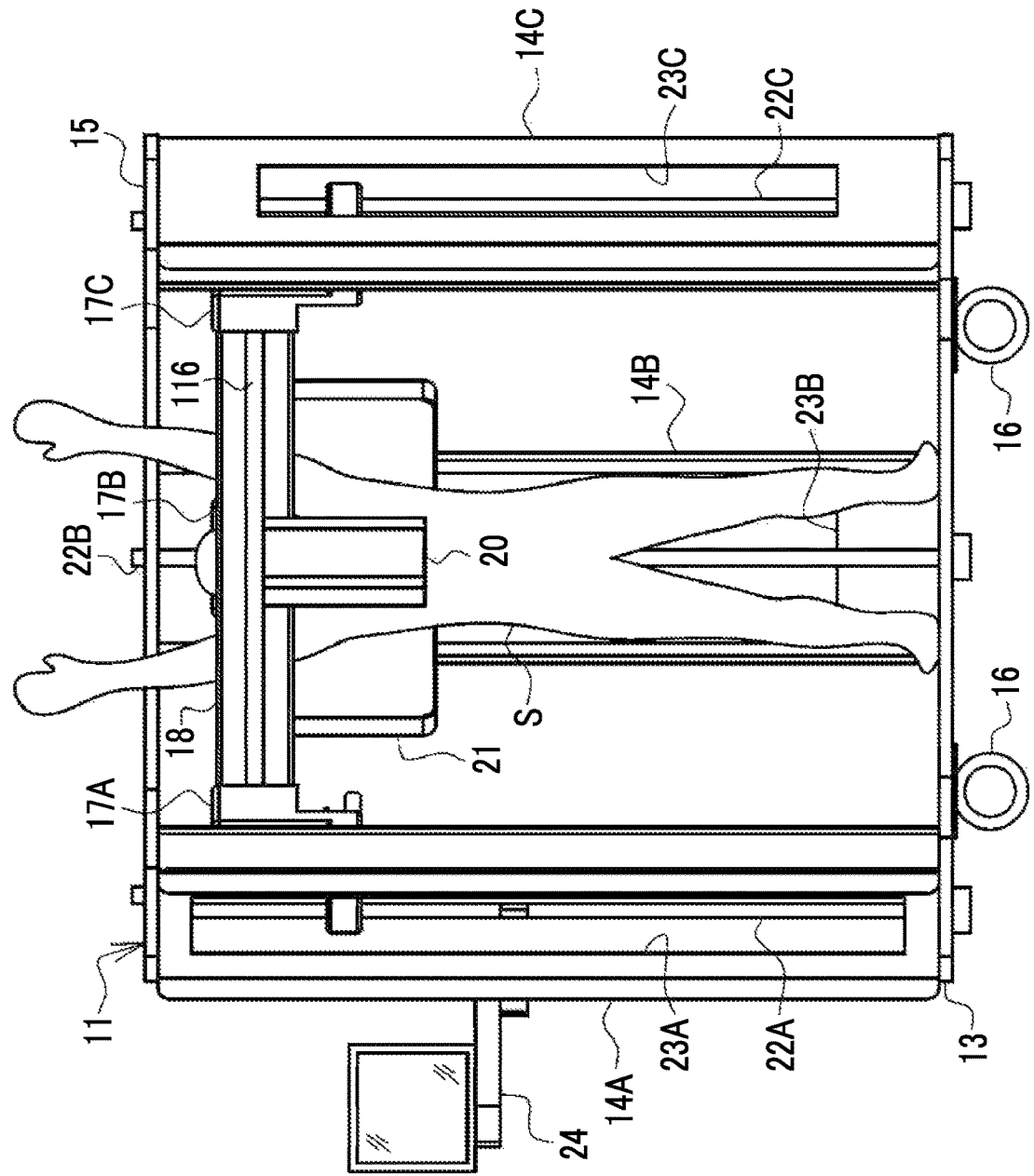
FIG. 2 is a front view illustrating an apparatus main body of the CT apparatus.
Figure 3:
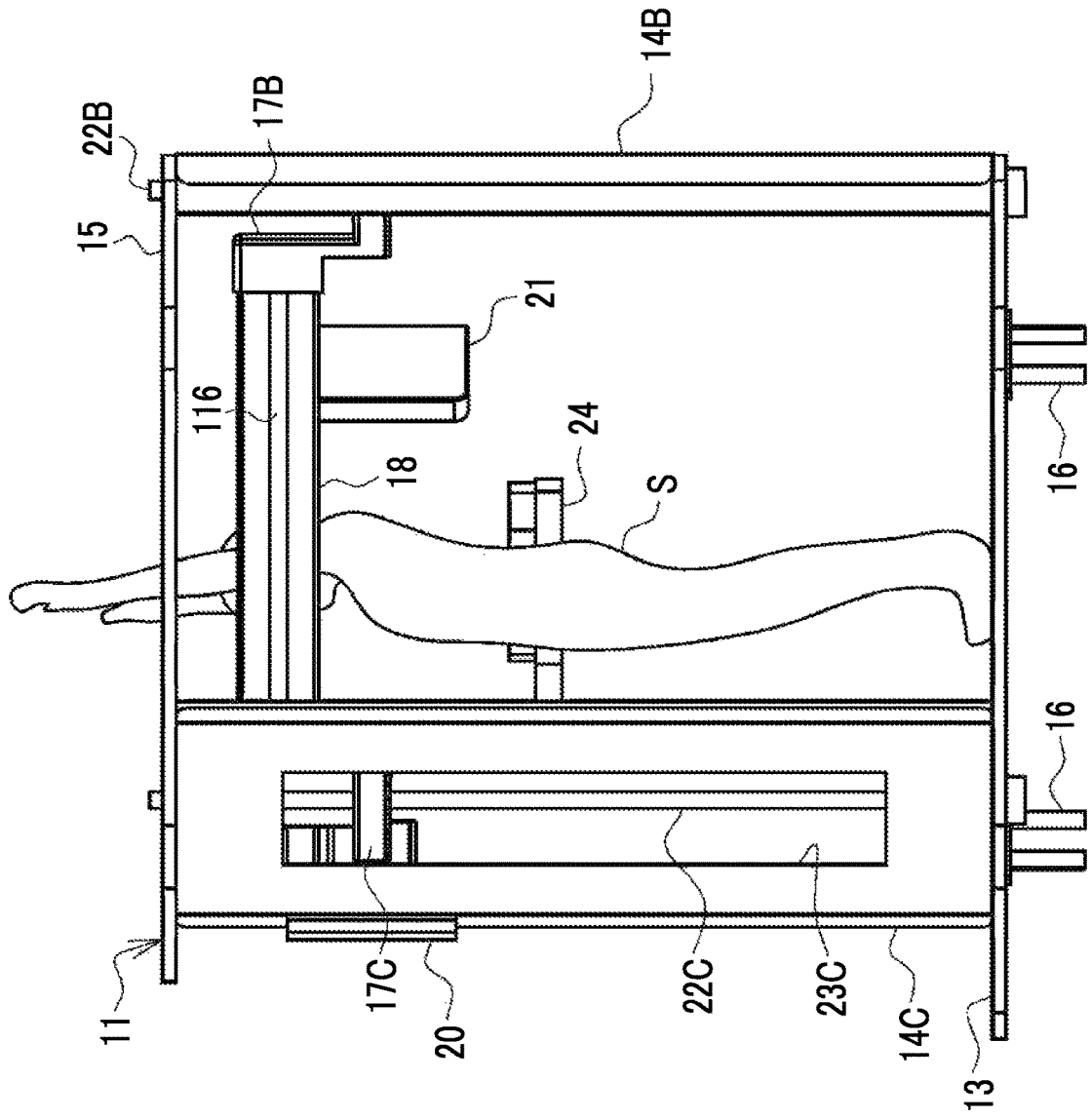
FIG. 3 is a side view illustrating the apparatus main body of the CT apparatus.

For example, as illustrated in FIG. 1, a CT apparatus 10 is an apparatus for obtaining a tomographic image TI (see FIG. 21) of a subject S and includes an apparatus main body 11 and a control device 12. The apparatus main body 11 is installed, for example, in a radiography room of a medical facility. The control device 12 is installed, for example, in a control room next to the radiography room. The control device 12 is a desktop personal computer, a notebook personal computer, or a tablet terminal. The CT apparatus 10 is an example of a "radiography apparatus" according to the technology of the present disclosure.

For example, as illustrated in FIGS. 1 to 4, the apparatus main body 11 comprises a stage 13, three columns 14A, 14B, and 14C, and a top plate 15. The stage 13 is an octagonal flat surface. Casters 16 for transportation are attached to four corners of a rear surface of the stage 13.

The caster 16 comprises a rotation lock mechanism (not illustrated). After the apparatus main body 11 is installed at an installation position, the rotation lock mechanism can be operated to lock the rotation of the caster 16. Alternatively, the caster 16 can be removed from the stage 13. The caster 16 can be removed after the apparatus main body 11 is installed at the installation position.

The outer shape of the columns 14A to 14C is a rectangular plate shape, and the columns 14A to 14C are vertically provided at four corners of the surface of the stage 13. The columns 14A and 14C are disposed on the front left and right sides of the apparatus main body 11 (the front left and right sides of the subject S). The column 14B is disposed at the center of the rear side of the apparatus main body 11 (behind the subject S). The top plate 15 is attached to the upper end portions of the columns 14A to 14C. The top plate 15 is an octagonal flat surface having an outer shape following the stage 13. The top plate 15 has a C-shape in which a central portion is hollowed out in a circular shape and a portion corresponding to the front side of the apparatus main body 11 between the columns 14A and 14C is cut out. Further, in the following description, the columns 14A to 14C are collectively referred to as columns 14 in a case in which they do not need to be distinguished from each other.

A connection member 17A is connected to the column 14A, a connection member 17B is connected to the column 14B, and a connection member 17C is connected to the column 14C. A frame 18 is connected to the connection members 17A to 17C. That is, the columns 14A to 14C and the frame 18 are connected to each other through the connection members 17A to 17C. Furthermore, in the following description, the connection members 17A to 17C are collectively referred to as connection members 17 in a case in which they do not need to be distinguished from each other.

The frame 18 has an annular shape. The subject S is positioned at a center C (see FIG. 4) of a cavity 19 of the annular frame 18. FIGS. 1 to 4 illustrate an aspect in which the subject S in a standing posture with both hands raised above the head is positioned.

The column 14 is provided with a guide rail (not illustrated) to which the connection member 17 is fitted. The connection member 17 and thus the frame 18 can be moved up and down in the vertical direction along the guide rail. That is, the columns 14 hold the frame 18 so as to be movable up and down in the vertical direction. In addition, the frame 18 can be rotated around the subject S using the center C as a central axis. That is, the columns 14A to 14C hold the frame 18 so as to be rotatable around the subject S. Further, the height position of the frame 18 may be changed by expanding and contracting the columns 14.

A radiation source 20 that emits radiation R (see FIG. 6), such as X-rays or $\gamma$-rays, and a radiation detector 21 that detects the radiation R are attached to the frame 18. Both the radiation source 20 and the radiation detector 21 protrude from a lower edge of the frame 18. The radiation source 20 and the radiation detector 21 are disposed at opposite positions (positions that are 180° away from each other) of the frame 18. The radiation source 20 has a box shape, and the radiation detector 21 has a pad shape. In a plan view of the frame 18 or the like from above, the radiation detector 21 has an arc surface shape that is convex toward the opposite side of the radiation source 20 and follows the shape of the frame 18. The arc surface shape is an example of a "U-shape" according to the technology of the present disclosure.

The column 14A is provided with a screw shaft 22A, the column 14B is provided with a screw shaft 22B, and the column 14C is provided with a screw shaft 22C. The screw shafts 22A to 22C have a height from the stage 13 to the top plate 15. The screw shafts 22A to 22C are rotated such that the connection members 17A to 17C and thus the frame 18 are moved up and down in the vertical direction. In addition, in the following description, the screw shafts 22A to 22C are collectively referred to as screw shafts 22 in a case in which they do not need to be distinguished from each other.

The column 14A has an opening 23A, the column 14B has an opening 23B, and the column 14C has an opening 23C. The openings 23A to 23C are formed by hollowing out most of the columns 14A to 14C in a rectangular shape, respectively. The subject S can be visually recognized from the outside of the apparatus main body 11 through the openings 23A to 23C. Each of the columns 14A to 14C partially looks like two columns because of each of the openings 23A to 23C. However, since the column is connected at the top and bottom of each of the openings 23A to 23C, the number is columns is one.

A touch panel display 25 is attached to the column 14A through a movable arm 24. The touch panel display 25 is operated by an operator of the CT apparatus 10 such as a radiology technician. Further, the touch panel display 25 displays various kinds of information to the operator.

Figure 4:
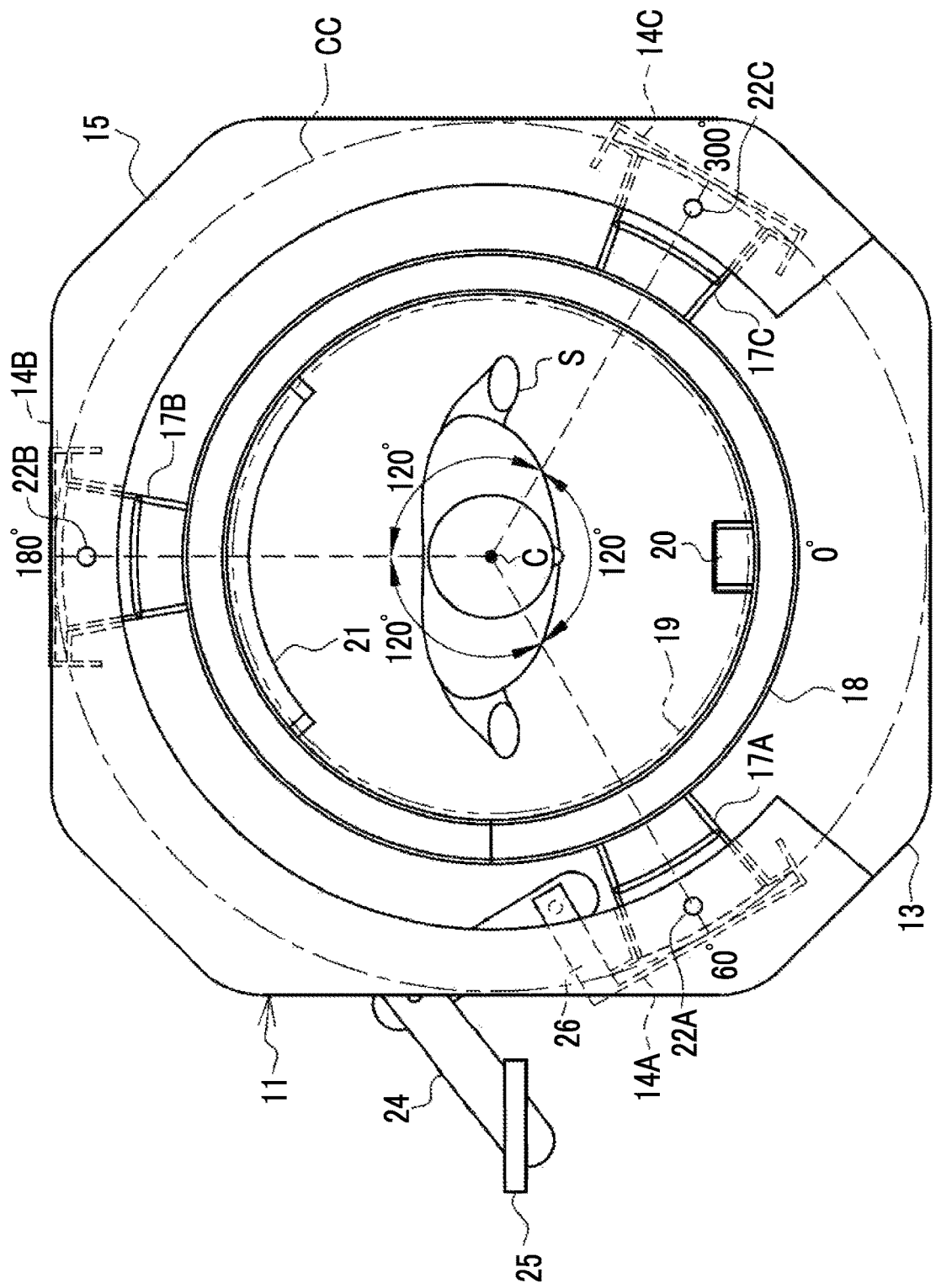
FIG. 4 is a top view illustrating the apparatus main body of the CT apparatus.

In FIG. 4 which is a plan view of the frame 18 and the like from above, in a case in which the position where the radiation source 20 is located in front of the apparatus main body 11 is set as a position of 0°, the column 14A is disposed at a position of 60° on a circle CC having the center C of the frame 18 as its center, the column 14B is disposed at a position of 180° on the circle CC, and the column 14C is disposed at a position of 300° on the circle CC. That is, the columns 14A to 14C are disposed at intervals of 120° on the circle CC. In addition, angles, such as "0°" and "60°", indicate, for example, "0°" and "60°" including an error (for example, an error of about 1% to 10%) that is generally allowed in the technical field to which the technology of the present disclosure belongs and does not depart from the gist of the technology of the present disclosure, in addition to perfect "0°" and "60°". Further, the term "equal interval" indicates an "equal interval" including an error (for example, an error of about 1% to 10%) that is generally allowed in the technical field to which the technology of the present disclosure belongs and does not depart from the gist of the technology of the present disclosure, in addition to a perfect "equal interval".

Figure 5:
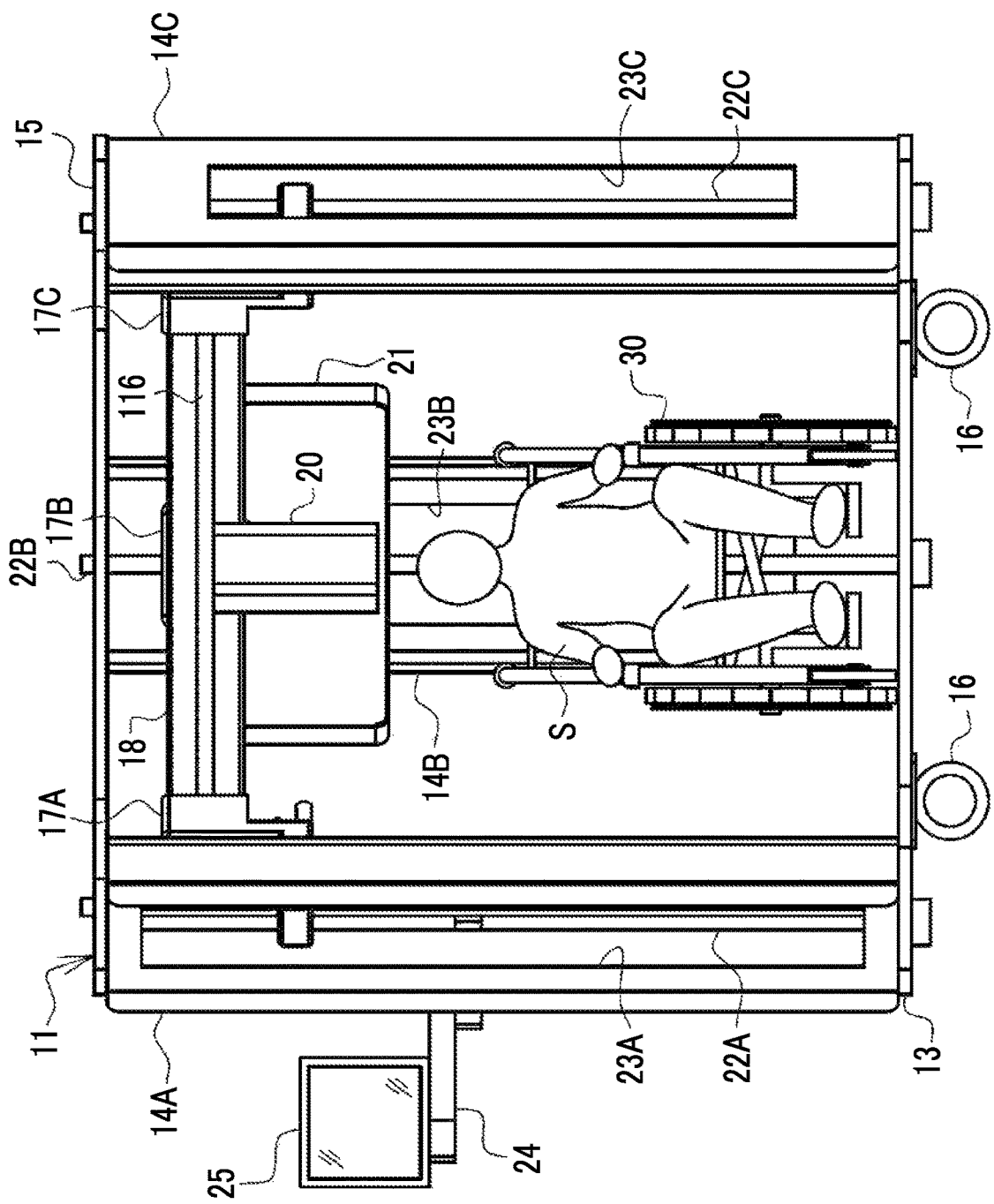
FIG. 5 is a front view illustrating the apparatus main body of the CT apparatus in a state in which a subject in a sitting posture on a wheelchair is positioned.

FIGS. 1 to 4 illustrate an example in which the subject S in a standing posture with both hands raised above the head is positioned in the cavity 19. However, the present disclosure is not limited to thereto. For example, as illustrated in FIG. 5, the CT apparatus 10 can image the subject S who is positioned in the cavity 19 in a sitting posture on a wheelchair 30. In addition, both the subject S in the standing posture and the subject S in the sitting posture on the wheelchair 30 are positioned so as to face the front at the position of 0°.

Figure 6:
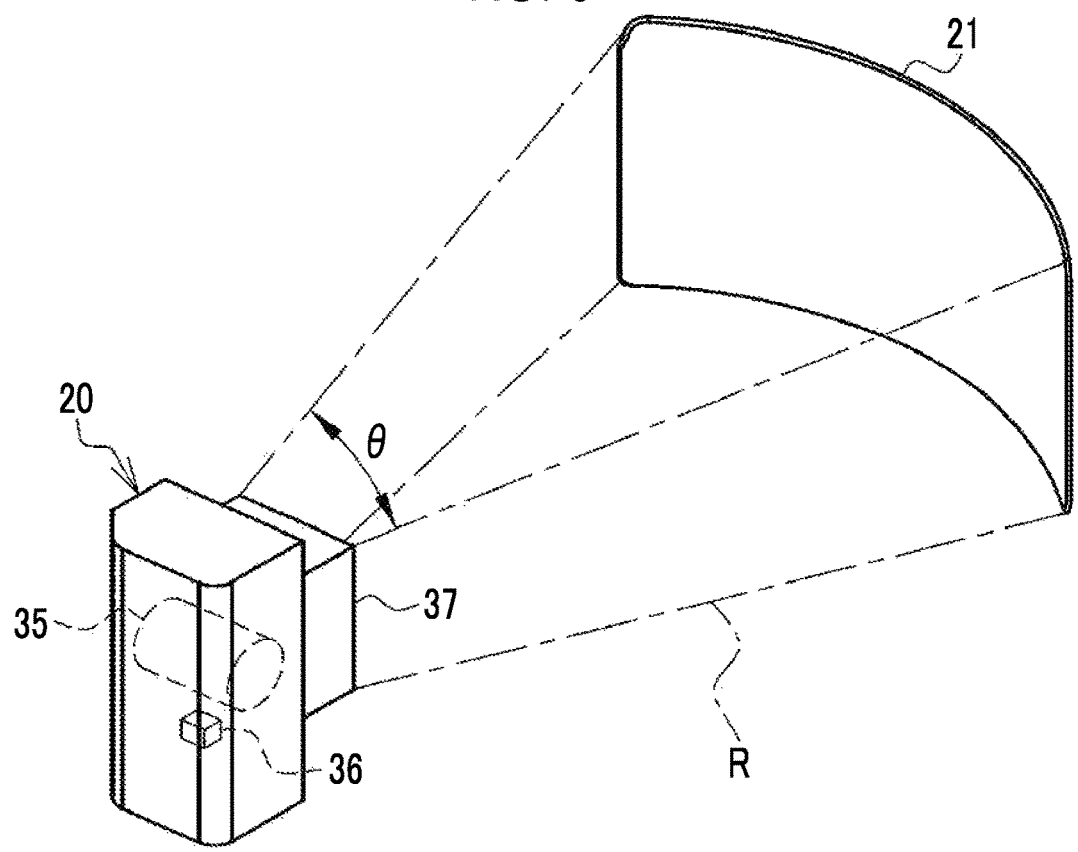
FIG. 6 is a perspective view illustrating a radiation source, a radiation detector, and radiation.

For example, as illustrated in FIG. 6, the radiation source 20 includes a radiation tube 35 and an irradiation field lamp 36. The radiation tube 35 emits the radiation R. The irradiation field lamp 36 emits, for example, orange visible light indicating the irradiation field of the radiation R.

Further, the radiation source 20 includes an irradiation field limiter 37. The irradiation field limiter 37 is also called a collimator and defines the irradiation field of the radiation R to the radiation detector 21. An incident opening through which the radiation R from the radiation tube 35 is incident and an exit opening through which the radiation R exits are formed in the irradiation field limiter 37. For example, four shielding plates are provided in the vicinity of the exit opening. The shielding plate is made of a material that shields the radiation R, for example, lead. The shielding plates are disposed on each side of a quadrangle, in other words, are assembled in a checkered pattern and form a quadrangular irradiation opening through which the radiation R is transmitted. The irradiation field limiter 37 changes the position of each shielding plate to change the size of the irradiation opening, thereby changing the irradiation field of the radiation R to the radiation detector 21. The radiation R having a quadrangular pyramid shape is emitted from the radiation source 20 by the operation of the irradiation field limiter 37. An irradiation angle θ of the radiation R is, for example, 45°.

Figure 7:
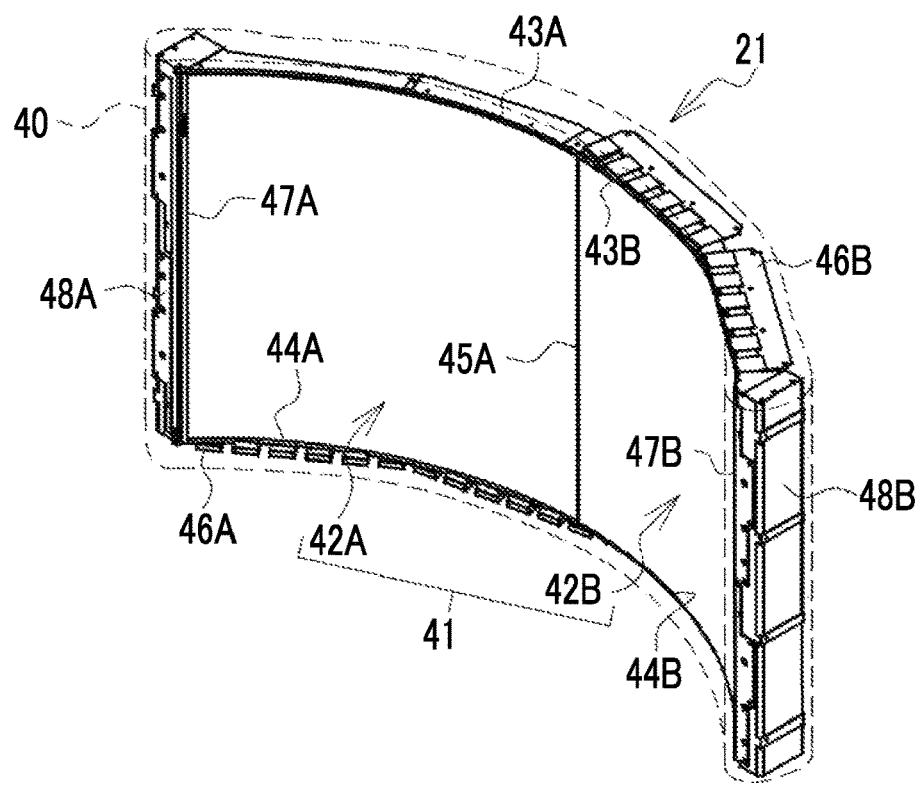
FIG. 7 is a perspective view illustrating the inside of the radiation detector.

For example, as illustrated in FIG. 7, the radiation detector 21 includes a housing 40 having an arc surface shape that follows the shape of the frame 18. The housing 40 is made of, for example, carbon. A sensor panel unit 41 is accommodated in the housing 40. The sensor panel unit 41 includes two sensor panels 42A and 42B using thin film transistors (hereinafter, abbreviated to TFTs). The sensor panels 42A and 42B have a square shape having a size of, for example, 17 inches (about 432 mm×about 432 mm). In the sensor panel 42A, opposite sides 43A and 44A are curved in an arc shape that follows the shape of the frame 18. Similarly, in the sensor panel 42B, opposite sides 43B and 44B are curved in an arc shape that follows the shape of the frame 18. The sensor panels 42A and 42B overlap each other on sides 45A and 45B that are not curved in an arc shape (see FIG. 8 and the like for the side 45B). In addition, the sensor panel unit 41 is an example of an "imaging sensor unit" according to the technology of the present disclosure. Further, the sensor panel 42A is an example of a "first imaging sensor" according to the technology of the present disclosure, and the sensor panel 42B is an example of a "second imaging sensor" according to the technology of the present disclosure.

A reading circuit board 46A is attached to the side 44A, and a reading circuit board 46B is attached to the side 43B. Nothing is attached to the side 43A facing the side 44A and the side 44B facing the side 43B. The sides 44A and 43B and thus the reading circuit boards 46A and 46B have a so-called two-fold symmetric relationship in which they are located at positions that are aligned with each other in a case in which they are rotated 180° about the center of the radiation detector 21. The reading circuit boards 46A and 46B are examples of a "circuit board" according to the technology of the present disclosure. Further, the sides 44A and 43B are examples of a "first side" according to the technology of the present disclosure, and the sides 43A and 44B are examples of a "second side" according to the technology of the present disclosure.

A switching circuit board 48A is attached to a side 47A facing the side 45A, and a switching circuit board 48B is attached to a side 47B facing the side 45B. The switching circuit boards 48A and 48B are also examples of the "circuit board" according to the technology of the present disclosure. In addition, similarly to the columns 14A to 14C, hereinafter, the sensor panels 42A and 42B and each component attached thereto may be represented by only numbers without letters "A" and "B".

Figure 8:
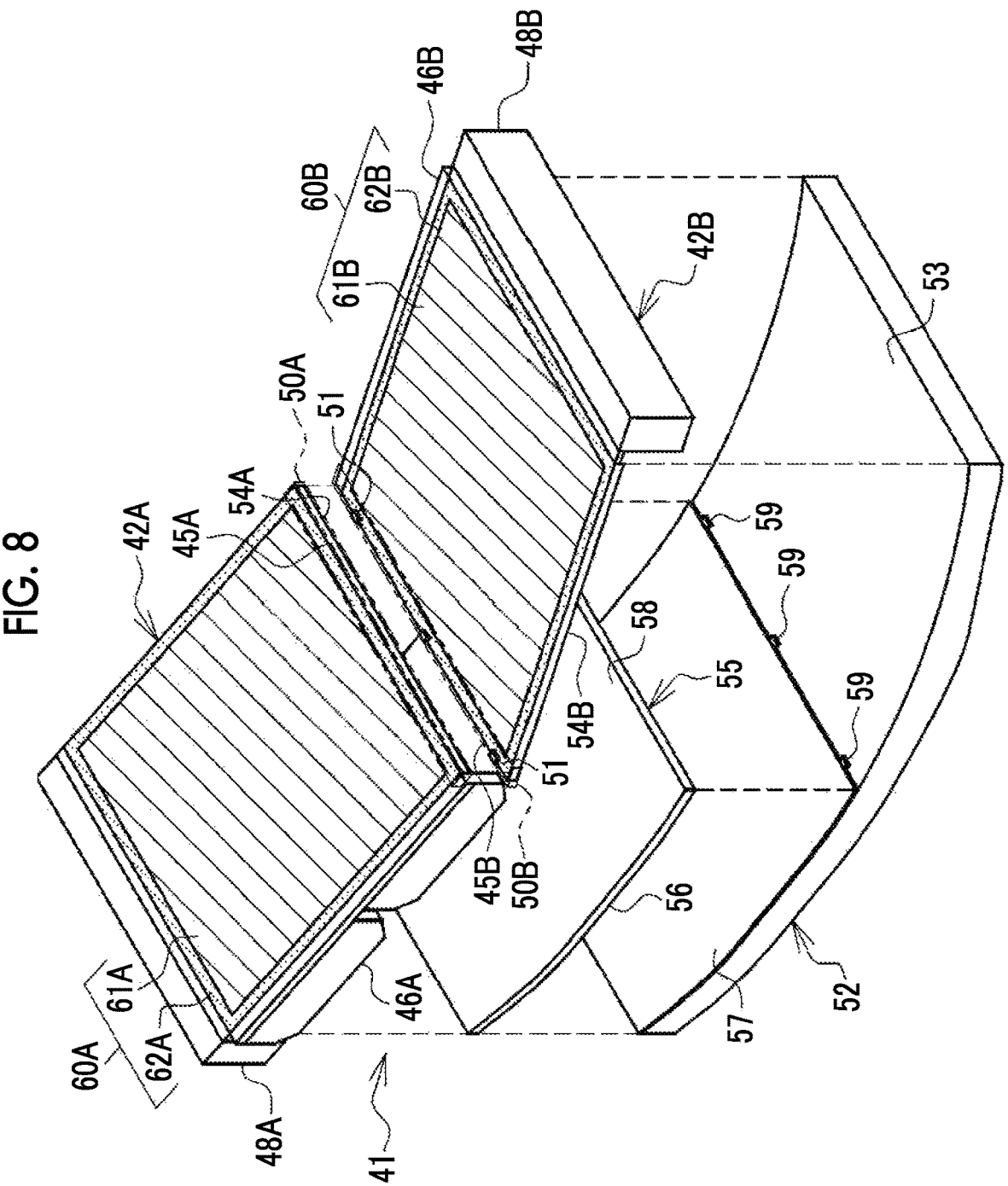
FIG. 8 is an exploded perspective view illustrating two sensor panels, a spacer, and a support table.
Figure 9:
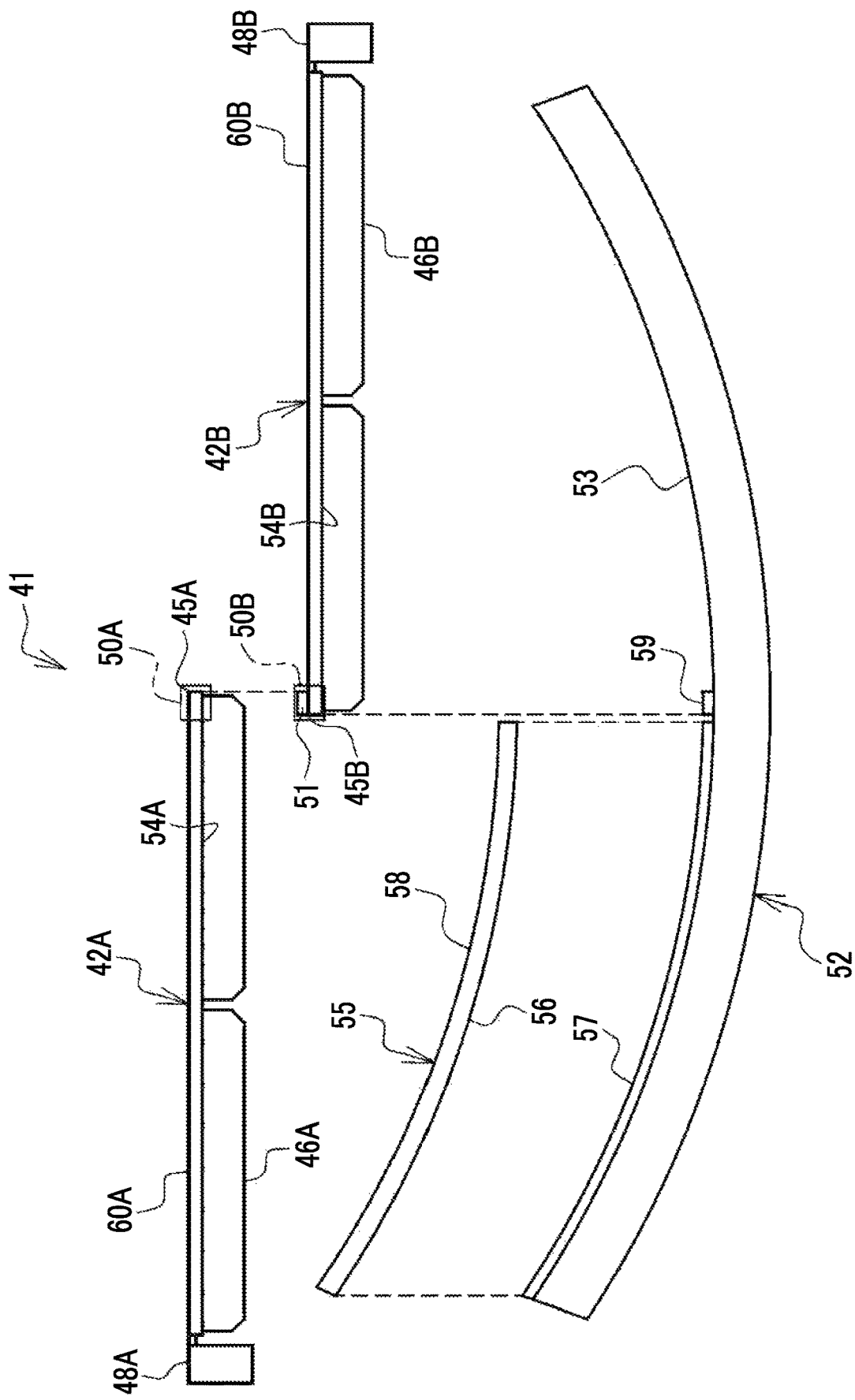
FIG. 9 is an exploded plan view illustrating the two sensor panels, the spacer, and the support table.

For example, as illustrated in FIGS. 8 and 9, in the sensor panels 42A and 42B, an end portion 50A on the side 45A and an end portion 50B on the side 45B are disposed so as to overlap each other in a thickness direction in a state in which the sides 45A and 45B are parallel to each other. The sensor panels 42A and 42B are disposed in the order of the sensor panel 42A and the sensor panel 42B as viewed from the radiation source 20. That is, the sensor panel 42A is disposed closer to the incident side of the radiation R than the sensor panel 42B in the thickness direction. Here, the term "parallel" indicates "parallel" including an error (for example, an error of about 1% to 10%) that is generally allowed in the technical field to which the technology of the present disclosure belongs and does not depart from the gist of the technology of the present disclosure, in addition to perfect "parallel". Further, the end portion 50A is an example of a "first end portion" according to the technology of the present disclosure, and the end portion 50B is an example of a "second end portion" according to the technology of the present disclosure.

The sensor panels 42A and 42B are fixed by rectangular fixing members 51 in the end portions 50A and 50B. Three fixing members 51 are disposed at equal intervals in the end portion 50B along the side 45B. That is, the fixing members 51 partially fix the sensor panels 42A and 42B. The fixing member 51 is, for example, a double-sided tape that is attached to the end portion 50B or an adhesive that is applied or mask-printed onto the end portion 50B. The fixing member 51 is an example of a "first fixing member" according to the technology of the present disclosure.

The sensor panel unit 41 is attached to a support table 52. The support table 52 is made of metal (see FIG. 13), such as aluminum or copper, and has an attachment surface 53 that is accurately processed in an arc surface shape (U-shape) which is convex toward the opposite side of the radiation source 20 so as to follow the shape of the frame 18. The sensor panel unit 41 is attached to the attachment surface 53 in a state in which it is curved following the arc surface shape. The curvature radius of the attachment surface 53 is, for example, 500 mm. A member (not illustrated) that is made of, for example, lead and shields the radiation R is attached to a surface of the support table 52 which is opposite to the attachment surface 53. Here, the "U-shape" is a shape in which the entire surface of the sensor panels 42A and 42B including imaging regions 61A and 61B, which will be described below, and the end portions 50A and 50B which overlap each other is curved. Specifically, the "U-shape" means a shape in which both end portions protrude toward one side and both end portions and a central portion are connected by a curved surface.

A spacer 55 is disposed between a first surface 54A of the sensor panel 42A and the attachment surface 53 of the support table 52. The spacer 55 is a thin plate that has substantially the same size as the sensor panel 42A and has an arc surface shape following the shape of the attachment surface 53. The spacer 55 has a thickness corresponding to the distance between the sensor panel 42A and the support table 52. In other words, the spacer 55 has a thickness that fills the step between the sensor panels 42A and 42B in the thickness direction caused by the overlap of the sensor panels 42A and 42B. The curvature radius of the sensor panel 42A is, for example, 500 mm, and the curvature radius of the sensor panel 42B is, for example, 501 mm. In this case, the step between the sensor panels 42A and 42B in the thickness direction is 1 mm, and the thickness of the spacer 55 is also 1 mm.

A first surface 56 of the spacer 55 is entirely attached to the attachment surface 53 by a fixing member 57, and a second surface 58 opposite to the first surface 56 faces the first surface 54A of the sensor panel 42A. The first surface 54A of the sensor panel 42A and the second surface 58 of the spacer 55 are in contact with each other, but are not fixed. Similarly to the fixing member 51, the fixing member 57 is, for example, a double-sided tape that is attached to the attachment surface 53 or an adhesive that is applied or mask-printed onto the attachment surface 53.

The first surface 54B of the sensor panel 42B is fixed to the attachment surface 53 in the end portion 50B by fixing members 59. Three fixing members 59 are disposed at equal intervals at positions corresponding to the fixing members 51 in a portion of the attachment surface 53 corresponding to the end portion 50B. That is, the fixing members 59 partially fix the sensor panel 42B (sensor panel unit 41) and the support table 52. Further, the fixing member 59 has the same size as the fixing member 51. Similarly to the fixing members 51 and 57, the fixing member 59 is, for example, a double-sided tape that is attached to the attachment surface 53 or an adhesive that is applied or mask-printed onto the attachment surface 53. The fixing member 59 is an example of a "second fixing member" according to the technology of the present disclosure. Furthermore, the term "same" in the "same position" and the "same size" indicates "same" including an error (for example, an error of about 1% to 10%) that is generally allowed in the technical field to which the technology of the present disclosure belongs and does not depart from the gist of the technology of the present disclosure, in addition to exact "same".

A second surface 60A of the sensor panel 42A which is opposite to the first surface 54A has an imaging region 61A which has a square shape and in which pixels 104A (see FIG. 13) are arranged and a non-imaging region 62A which has a rectangular ring shape and surrounds the imaging region 61A and in which the pixels 104A are not arranged. Similarly, a second surface 60B of the sensor panel 42B which is opposite to the first surface 54B has an imaging region 61B and a non-imaging region 62B. The imaging region 61A is an example of a "first imaging region" according to the technology of the present disclosure, and the imaging region 61B is an example of a "second imaging region" according to the technology of the present disclosure.

Figure 10:
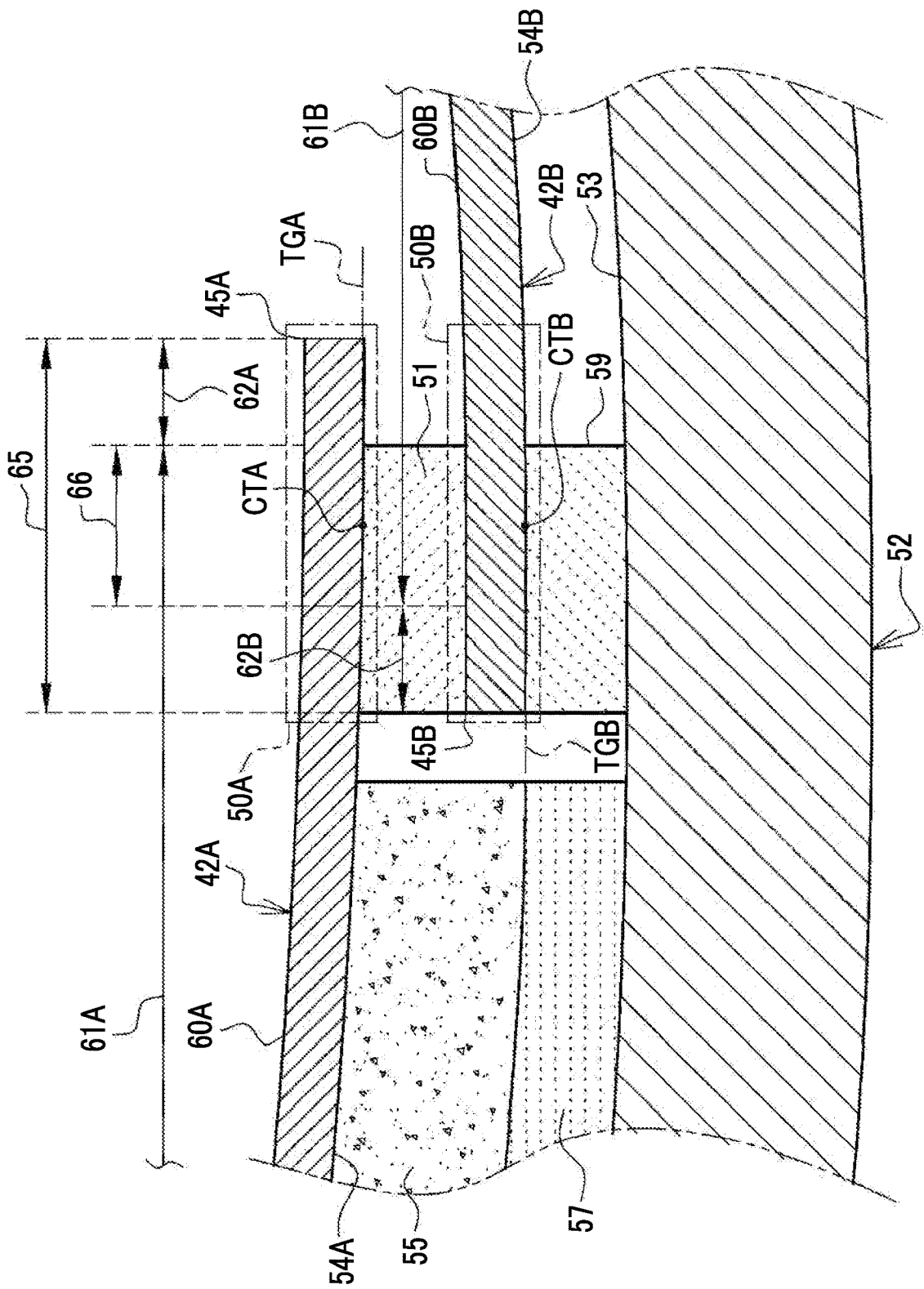
FIG. 10 is a cross-sectional view illustrating the vicinity of an overlap region of end portions of the two sensor panels.

For example, as illustrated in FIG. 10, the fixing members 51 fix the sensor panel 42A and the sensor panel 42B in an overlap region 65 in which the end portion 50A and the end portion 50B overlap each other. Similarly, the fixing members 59 fix the sensor panel 42B and the support table 52 in the overlap region 65. The fixing members 51 and 59 are not disposed in a region other than the overlap region 65. The overlap region 65 is a region defined by an end of the sensor panel 42A on the side 45A and an end of the sensor panel 42B on the side 45B.

As described above, the fixing member 59 is disposed at the same position as the fixing member 51 and has the same size as the fixing member 51. Therefore, the fixing member 59 entirely overlaps the fixing member 51 in the overlap region 65 in a plan view of the sensor panel unit 41 in the thickness direction. In addition, the fixing member 59 may at least partially overlap the fixing member 51 in the overlap region 65.

The imaging region 61A of the sensor panel 42A and the imaging region 61B of the sensor panel 42B overlap each other in the overlap region 65 in a plan view of the sensor panel unit 41 in the thickness direction. The fixing member 51 is disposed at a position that does not protrude from an overlap imaging region 66, in which the imaging regions 61A and 61B overlap each other, toward the imaging region 61B (non-imaging region 62A).

The end portion 50A of the sensor panel 42A and the end portion 50B of the sensor panel 42B are parallel to each other. Specifically, a tangent line TGA between the sensor panel 42A and the fixing member 51 is parallel to a tangent line TGB between the sensor panel 42B and the fixing member 59. The tangent line TGA is a point in a fixing region of the fixing member 51 to the sensor panel 42A, and a point intersecting a center line of the overlap region 65 is referred to as a contact point CTA. The tangent line TGB is a point in a fixing region of the fixing member 59 to the sensor panel 42B, and a point intersecting the center line of the overlap region 65 is referred to as a contact point CTB.

Further, for example, in FIG. 10, for convenience, the thickness of the fixing members 51, 57, and 59 is exaggerated to be larger than that of the sensor panel 42. However, in practice, the thickness of at least the fixing members 57 and 59 among the fixing members 51, 57, and 59 is significantly smaller than the thickness of the sensor panel 42. Therefore, the first surface 54B of the sensor panel 42B comes into contact with the attachment surface 53 except the end portion 50B, and the sensor panel 42B is attached in a shape that follows the attachment surface 53.

Figure 11:
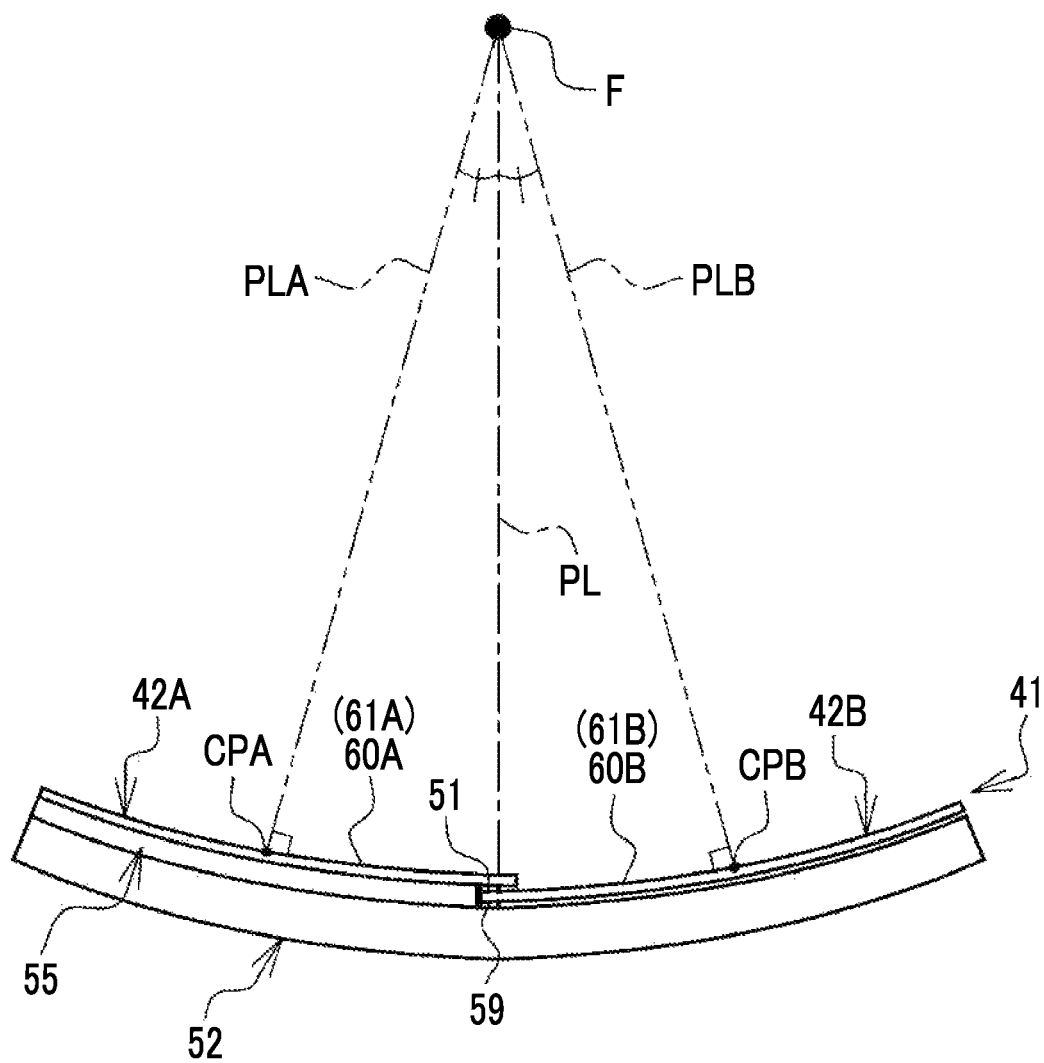
FIG. 11 is a diagram illustrating a positional relationship between a focus of the radiation and the sensor panels.

For example, as illustrated in FIG. 11, a perpendicular line PLA drawn from the focus F of the radiation R to the second surface 60A of the sensor panel 42A intersects a center point CPA of the imaging region 61A. Similarly, a perpendicular line PLB drawn from the focus F to the second surface 60B of the sensor panel 42B intersects a center point CPB of the imaging region 61B. The perpendicular lines PLA and PLB have the same length and have the same angle with respect to a perpendicular line PL drawn from the focus F to a center point of the sensor panel unit 41. Therefore, the centers of the arc surfaces (centers of curvature) of the sensor panels 42A and 42B are aligned with each other at the focus F. Further, the sensor panels 42A and 42B are substantially mirror-symmetric with respect to the perpendicular line PL.

Since the sensor panels 42A and 42B have the same basic configuration such as the same attachment structure, the sensor panel 42A will be mainly described below.

Figure 12:
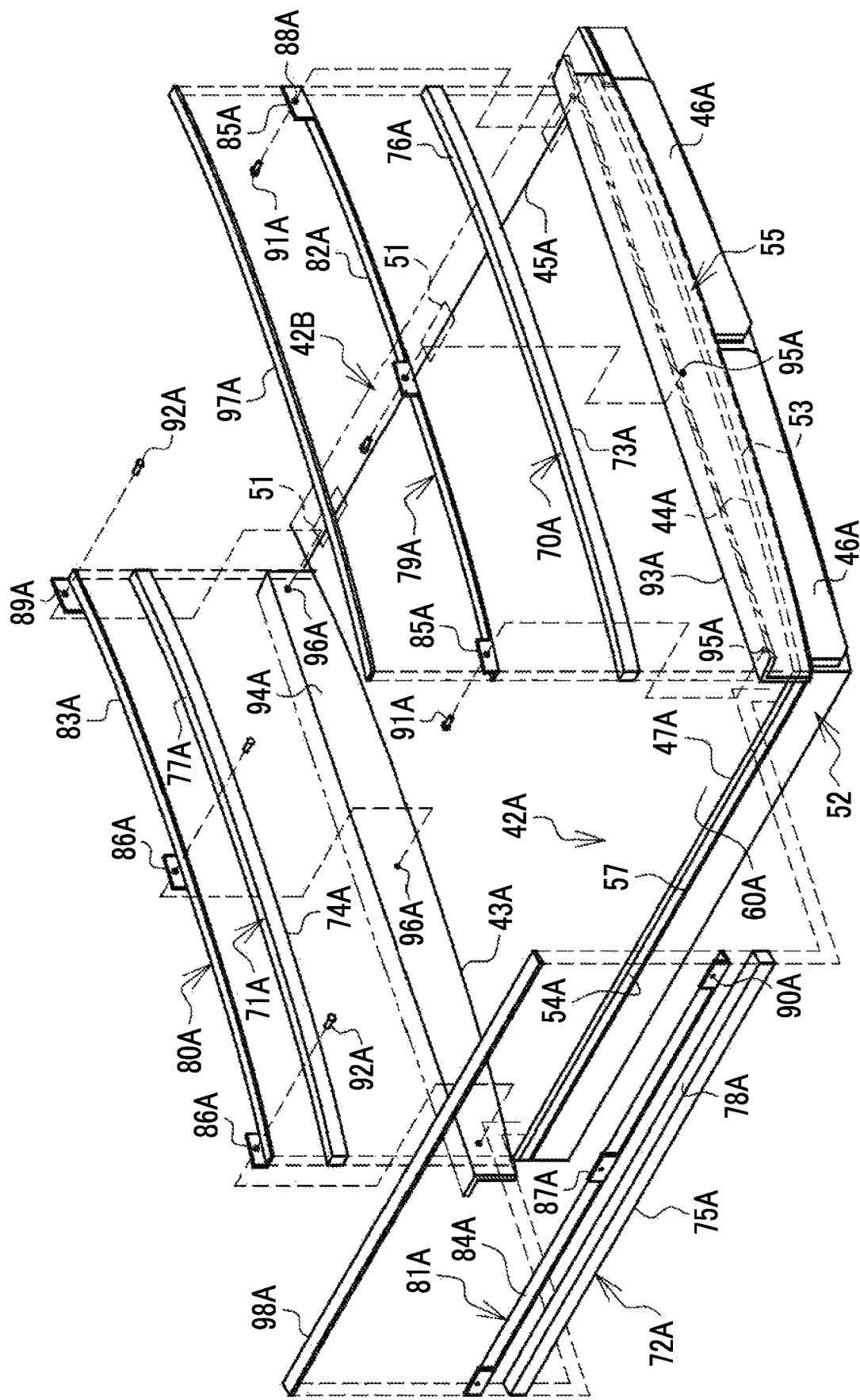
FIG. 12 is a perspective view illustrating an attachment structure of the sensor panel.

For example, as illustrated in FIG. 12, contact members 70A, 71A, and 72A come into contact with the second surface 60A of the sensor panel 42A. The contact members 70A to 72A have an elongated square column shape. The contact members 70A to 72A are elastic bodies made of various kinds of rubber, such as silicone rubber, nitrile rubber (NBR), and urethane rubber, various elastomers, various flexible resins, such as nylon and vinyl chloride, or various foams, such as foamed polyethylene, foamed acrylic, and foamed urethane. In addition, in FIG. 12, the switching circuit board 48A is not illustrated in order to avoid complication.

The contact members 70A to 72A suppress the lifting of the sensor panel 42A from the support table 52. Specifically, the contact member 70A has substantially the same length as the side 44A and comes into contact with the end portion of the sensor panel 42A on the side 44A to suppress the lifting of the end portion of the sensor panel 42A on the side 44A from the support table 52. The contact member 71A has substantially the same length as the side 43A and comes into contact with the end portion of the sensor panel 42A on the side 43A to suppress the lifting of the end portion of the sensor panel 42A on the side 43A from the support table 52. The contact member 72A has a slightly smaller length than the side 47A and comes into contact with the end portion of the sensor panel 42A on the side 47A to suppress the lifting of the end portion of the sensor panel 42A on the side 47A from the support table 52.

A surface 73A (hereinafter, referred to as a contact surface 73A) of the contact member 70A which comes into contact with the second surface 60A has an arc surface shape that follows the arcuate shape of the side 44A. Similarly, a surface 74A (hereinafter, referred to as a contact surface 74A) of the contact member 71A which comes into contact with the second surface 60A has an arc surface shape that follows the arcuate shape of the side 43A. In addition, the contact members 70A and 71A have a shape that follows the arcuate shape of the sides 44A and 43A as a whole. On the other hand, a surface 75A (hereinafter, referred to as a contact surface 75A) of the contact member 72A which comes into contact with the second surface 60A and thus the contact member 72A have a straight shape that follows the linear shape of the side 47A.

A holding member 79A is attached to a surface 76A of the contact member 70A which is opposite to the contact surface 73A. Similarly, a holding member 80A is attached to a surface 77A of the contact member 71A which is opposite to the contact surface 74A. In addition, a holding member 81A is attached to a surface 78A of the contact member 72A which is opposite to the contact surface 75A.

The holding members 79A to 81A hold the contact members 70A to 72A while pressing the contact members 70A to 72A against the sensor panel 42A, respectively. The holding members 79A to 81A are made of a material having a higher rigidity than the contact members 70A to 72A, for example, metal such as aluminum or copper. Since the contact members 70A to 72A are elastic bodies as described above, they are held by the holding members 79A to 81A while being pressed against the sensor panel 42A to bias the sensor panel 42A to the attachment surface 53.

The holding member 79A has a main body portion 82A and three attachment pieces 85A. Similarly, the holding member 80A has a main body portion 83A and three attachment pieces 86A. In addition, the holding member 81A has a main body portion 84A and three attachment pieces 87A. Similarly to the contact members 70A and 71A, the main body portions 82A and 83A have a shape that follows the arcuate shape as a whole. On the other hand, the main body portion 84A has a straight shape as a whole similarly to the contact member 72A.

The attachment pieces 85A are portions that protrude from both end portions and a central portion of the main body portion 82A to the side opposite to the contact member 70A at a right angle. The attachment pieces 86A are portions that protrude from both end portions and a central portion of the main body portion 83A to the side opposite to the contact member 71A at a right angle. Further, the attachment piece 87A are portions that protrude from both end portions and a central portion of the main body portion 84A to the side opposite to the contact member 72A at a right angle. A screw insertion hole 88A is formed in the attachment piece 85A. A screw insertion hole 89A is formed in the attachment piece 86A. Further, a screw insertion hole 90A is formed in the attachment piece 87A. A screw 91A is inserted into the screw insertion hole 88A. A screw 92A is inserted into the screw insertion hole 89A. Further, a screw (not illustrated) is inserted into the screw insertion hole 90A.

The screw 91A inserted into the screw insertion hole 88A is inserted into a screw hole 95A of an attachment frame 93A that is provided in the support table 52. Therefore, the holding member 79A is fastened and fixed to the attachment frame 93A. The contact member 70A is held while being sandwiched between the holding member 79A and the second surface 60A. The screw 92A inserted into the screw insertion hole 89A is inserted into a screw hole 96A of an attachment frame 94A that is provided in the support table 52. Therefore, the holding member 80A is fastened and fixed to the attachment frame 94A. The contact member 71A is held while being sandwiched between the holding member 80A and the second surface 60A. Further, the screw inserted into the screw insertion hole 90A is inserted into a screw hole (not illustrated) of an attachment frame (not illustrated) that is provided in the support table 52. Therefore, the holding member 81A is fastened and fixed to the attachment frame. The contact member 72A is held while being sandwiched between the holding member 81A and the second surface 60A.

A radiation shielding member 97A is attached to a surface of the main body portion 82A which is irradiated with the radiation R. In addition, a radiation shielding member 98A is attached to a surface of the main body portion 84A which is irradiated with the radiation R. The radiation shielding members 97A and 98A are made of a material that shields the radiation R, for example, lead. The radiation shielding member 97A prevents the reading circuit board 46A from being irradiated with the radiation R to protect the reading circuit board 46A. The radiation shielding member 98A prevents the switching circuit board 48A from being irradiated with the radiation R to protect the switching circuit board 48A.

Figure 13:
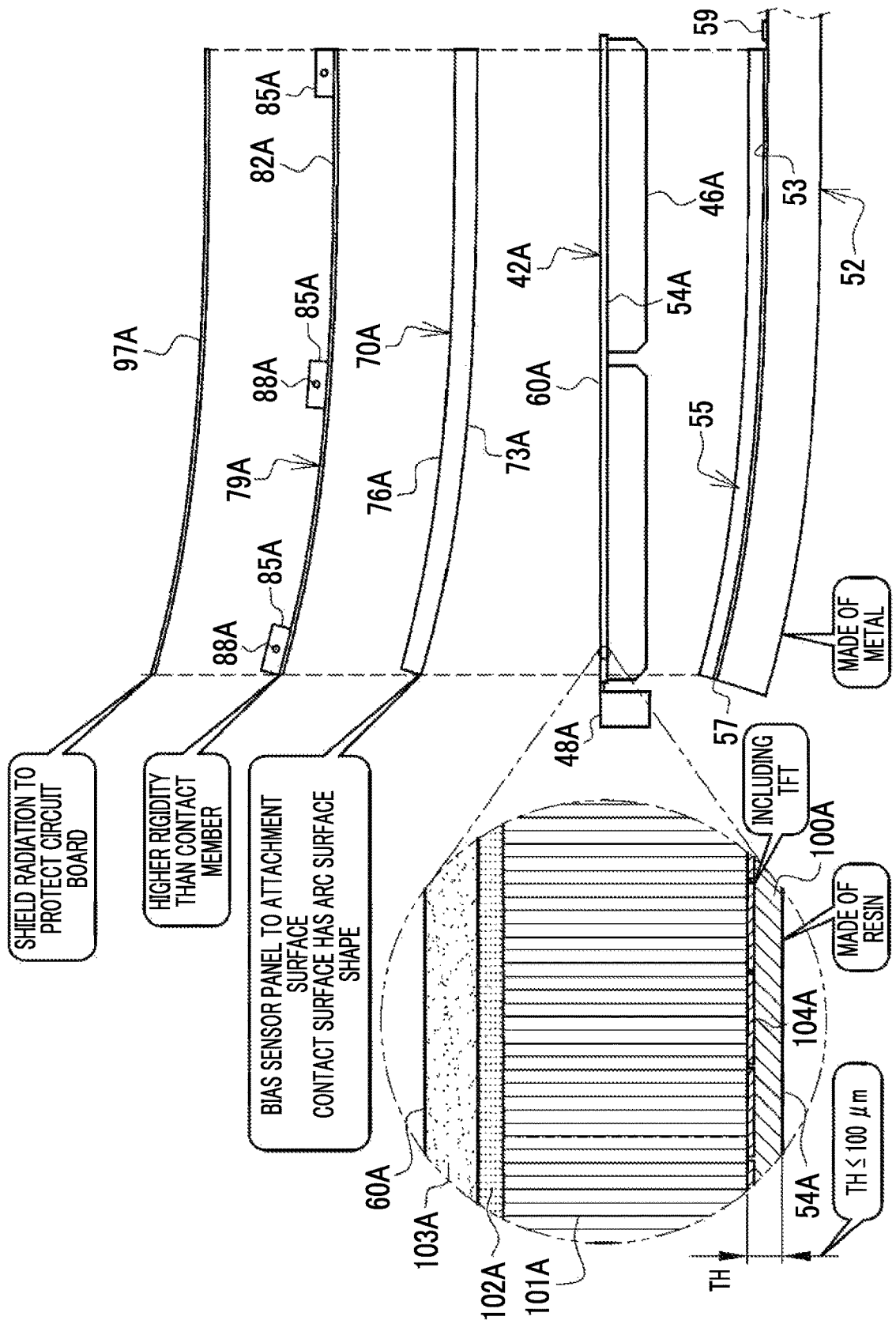
FIG. 13 is a plan view illustrating the attachment structure of the sensor panel and a detailed configuration of the sensor panel.

In FIG. 13, the sensor panel 42A has a substrate 100A and a scintillator 101A. The scintillator 101A includes, for example, terbium-activated gadolinium oxysulfide (GOS; $Gd_2O_2S$:Tb) and converts the radiation R into visible light. The scintillator 101A is attached to a support 103A through a pressure-sensitive adhesive layer 102A. The support 103A is made of, for example, white polyethylene terephthalate (PET). A rear surface of the substrate 100A is the first surface 54A, and a front surface of the support 103A is the second surface 60A.

The substrate 100A is a flexible thin film sheet that is made of a resin such as polyimide. The substrate 100A includes fine particles of an inorganic oxide that absorbs backscattered rays. Examples of the inorganic oxide include silicon dioxide ($SiO_2$), magnesium oxide (MgO), aluminum oxide (so-called alumina, $Al_2O_3$), and titanium oxide ($TIO_2$). An example of the substrate 100A having the above-mentioned features is XENOMAX (registered trademark) manufactured by Xenomax Japan Co., Ltd. A thickness TH of the substrate 100A is equal to or less than 100 μm. The thickness TH is more preferably equal to or greater than 20 μm and less than 50 μm ($20 \leq TH < 50$).

The substrate 100A is provided with the pixels 104A that detect the visible light converted from the radiation R by the scintillator 101A. As is well known, the pixel 104A includes a light receiving unit that senses the visible light and generates charge and a TFT as a switching element that reads out the charge accumulated in the light receiving unit. A plurality of signal lines for inputting the charge of the light receiving units to the reading circuit board 46A and a plurality of scanning lines for giving on/off signals (scanning signals) from the switching circuit board 48A to the TFTs are provided on the substrate 100A so as to intersect each other in the vertical and horizontal directions. The pixels 104A are disposed at the intersections of the plurality of signal lines and scanning lines. That is, the pixels 104A are two-dimensionally arranged. In addition, the pixel 104A may not sense the visible light converted from the radiation R, but may directly sense the radiation R to generate charge.

The pitch of the pixels 104A is, for example, 150 μm. In addition, the regions fixed by the fixing members 51 and 59 have a size that does not cause a deviation equal to or more than the pitch of the pixels 104 between the sensor panel unit 41 and the support table 52 due to thermal expansion or contraction of the sensor panel unit 41. Further, the positions fixed by the fixing members 51 and 59 have a distance that does not cause a deviation equal to or more than the pitch of the pixels 104 between the sensor panel unit 41 and the support table 52 due to thermal expansion or contraction of the sensor panel unit 41.

Figure 14:
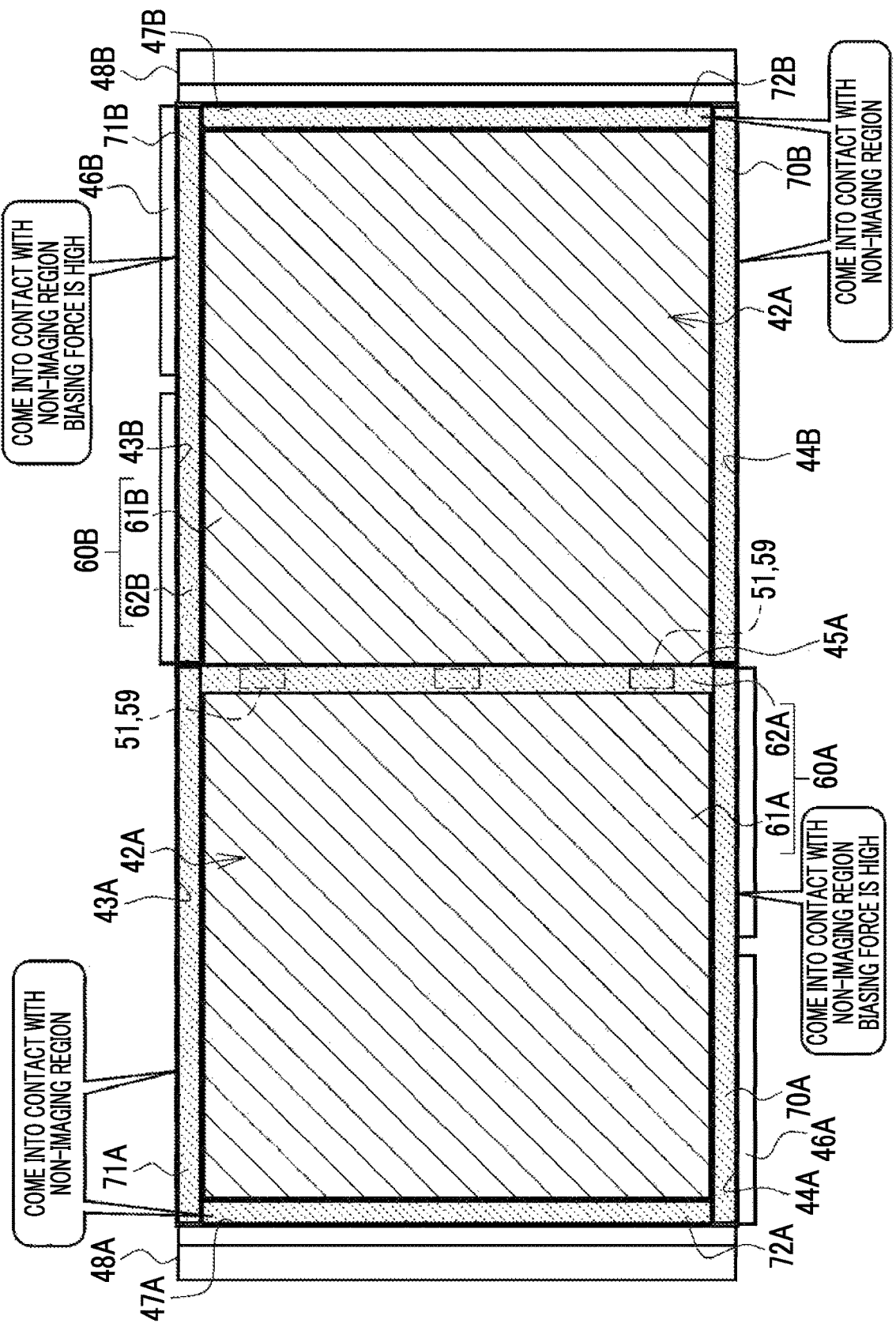
FIG. 14 is a plan view illustrating contact positions of contact members.

As illustrated in FIG. 14 in a state in which the holding members 79A to 81A and the like are removed, all of the contact members 70A to 72A come into contact with the non-imaging region 62A. Similarly, the contact members 70B, 71B, and 72B that suppress the lifting of the sensor panel 42B from the support table 52 come into contact with the non-imaging region 62B.

The contact member 70B has substantially the same length as the side 44B and comes into contact with the end portion of the sensor panel 42B on the side 44B to suppress the lifting of the end portion of the sensor panel 42B on the side 44B from the support table 52. The contact member 71B has substantially the same length as the side 43B and comes into contact with the end portion of the sensor panel 42B on the side 43B to suppress the lifting of the end portion of the sensor panel 42B on the side 43B from the support table 52. The contact member 72B has a slightly shorter length than the side 47B and comes into contact with the end portion of the sensor panel 42B on the side 47B to suppress the lifting of the end portion of the sensor panel 42B on the side 47B from the support table 52.

The contact member 70A has a higher biasing force than the contact member 71A. Further, the contact member 71B has a higher biasing force than the contact member 70B. The contact members 70A and 71B are examples of a "first contact member" according to the technology of the present disclosure. In addition, the contact members 71A and 70B are examples of a "second contact member" according to the technology of the present disclosure.

As a method for increasing the biasing force, for example, a method can be adopted which increases the amount of pressing of the contact members 70A and 71B to be larger than the amount of pressing of the contact members 71A and 70B. For example, in a case in which the contact members 71A and 70B with a thickness of 10 mm are pressed to 8 mm, the contact members 70A and 71B are pressed from 10 mm to 6 mm. Alternatively, a method may be used in which the elastic force of the contact members 70A and 71B is higher than the elastic force of the contact members 71A and 70B.

Figure 15:
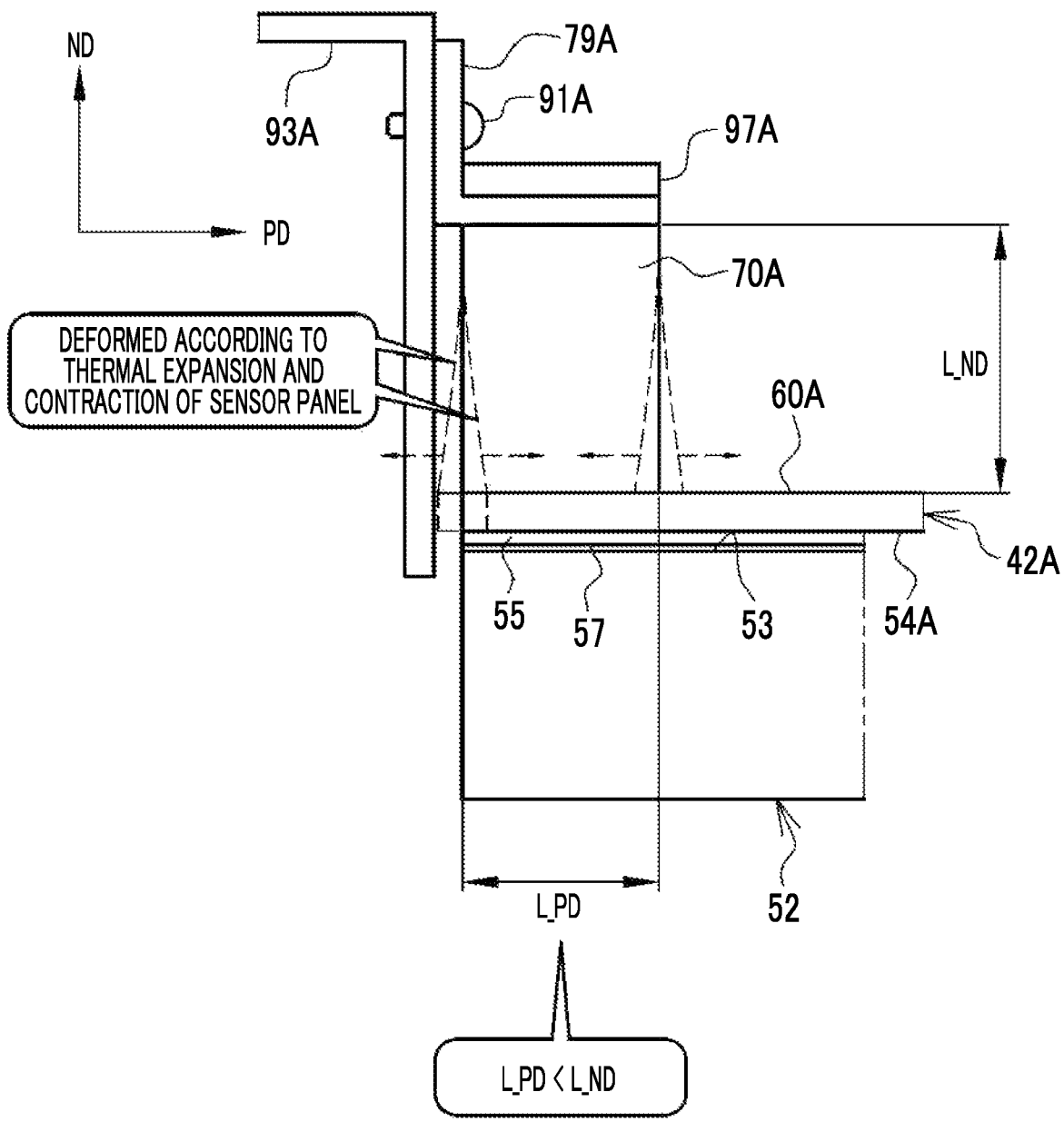
FIG. 15 is a diagram illustrating the degree of deformation and the size of the contact member.

For example, as illustrated in FIG. 15, as represented by a broken line, the sensor panel 42A is thermally expanded and contracted in a direction (hereinafter, referred to as a plane direction) PD parallel to the attachment surface 53 due to heat during driving. The contact member 70A is deformed (shear-deformed) as represented by the broken line according to the thermal expansion and contraction of the sensor panel 42A.

In the contact member 70A, a second length L_PD along a plane direction PD is smaller than a first length L_ND along a normal direction ND to the attachment surface 53 (L_PD<L_ND). In addition, the contact member 70A has been described as an example in FIG. 15. However, the contact members 71A, 72A, and 70B to 72B are also deformed according to the thermal expansion and contraction of the sensor panels 42A and 42B. Further, in the contact members 71A, 72A, and 70B to 72B, the second length L_PD along the plane direction PD is smaller than the first length L_ND along the normal direction ND to the attachment surface 53.

Figure 16:
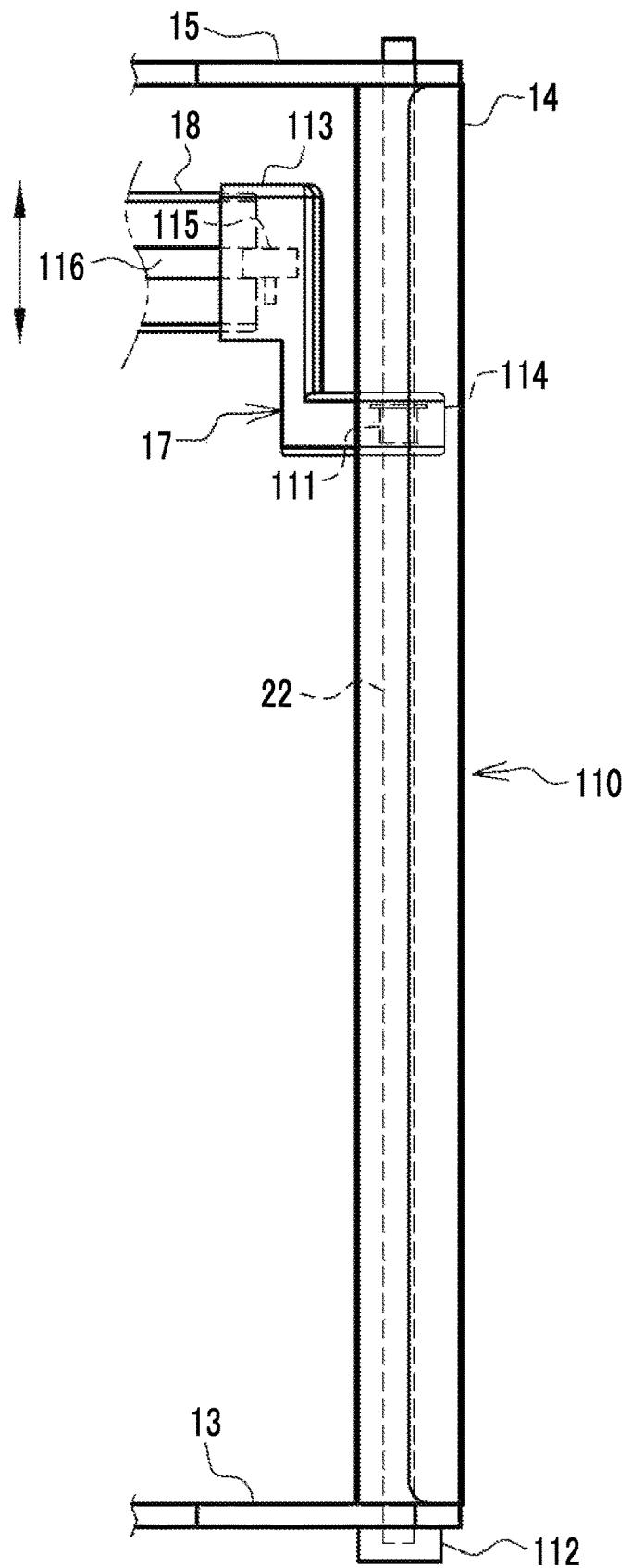
FIG. 16 is a diagram illustrating an elevating mechanism.

For example, as illustrated in FIG. 16, an elevating mechanism 110 that raises and lowers the connection member 17 and thus the frame 18 in the vertical direction is a ball screw mechanism including, for example, the screw shaft 22, a nut 111 that has a ball provided therein and is engaged with the screw shaft 22, an elevating motor 112 that rotates the screw shaft 22. The elevating motor 112 is attached to the rear surface of the stage 13. The height position of the frame 18 is determined from the rotation direction and rotation speed of the elevating motor 112.

The connection member 17 has a first connection portion 113 that is connected to the frame 18 and a second connection portion 114 that is connected to the column 14. The first connection portion 113 protrudes toward the frame 18, and the second connection portion 114 protrudes toward the column 14. The connection member 17 has a Z-shape as a whole. A bearing 115 is provided in the first connection portion 113. The bearing 115 is fitted to a guide groove 116 (see also FIG. 1 and the like) that is formed over the entire circumference of the frame 18. The bearing 115 rolls as the frame 18 is rotated. The nut 111 is provided in the second connection portion 114.

Figure 17:
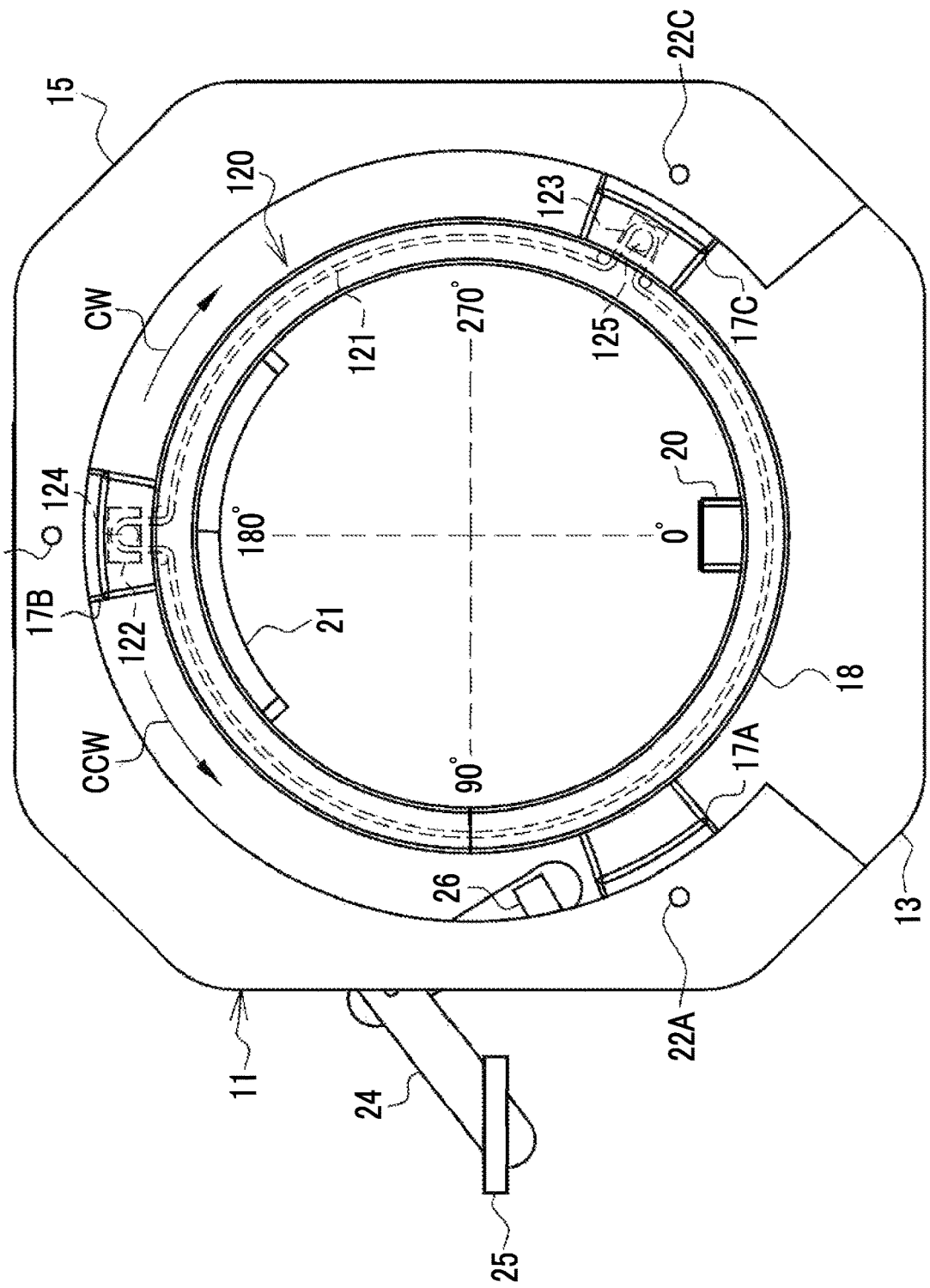
FIG. 17 is a diagram illustrating a rotation mechanism.

For example, as illustrated in FIG. 17, a rotation mechanism 120 that rotates the frame 18 around the subject S includes a rotation belt 121 that is wound around the entire circumference of the frame 18, a rotary motor 122, a potentiometer 123, and the like. The rotary motor 122 is provided in the connection member 17B and is connected to a portion of the rotation belt 121 drawn out from the frame 18 through a pulley 124. The rotary motor 122 is driven to rotate the frame 18 in a clockwise (right-hand rotation) direction CW and a counterclockwise (left-hand rotation) direction CCW. The potentiometer 123 is provided in the connection member 17C and is connected to a portion of the rotation belt 121 drawn out from the frame 18 through the pulley 125. The potentiometer 123 has a variable resistor whose resistance value is changed depending on the rotation position of the frame 18 and outputs a voltage signal corresponding to the rotation position of the frame 18. The rotation position of the frame 18 is determined by the voltage signal from the potentiometer 123.

Figure 18:
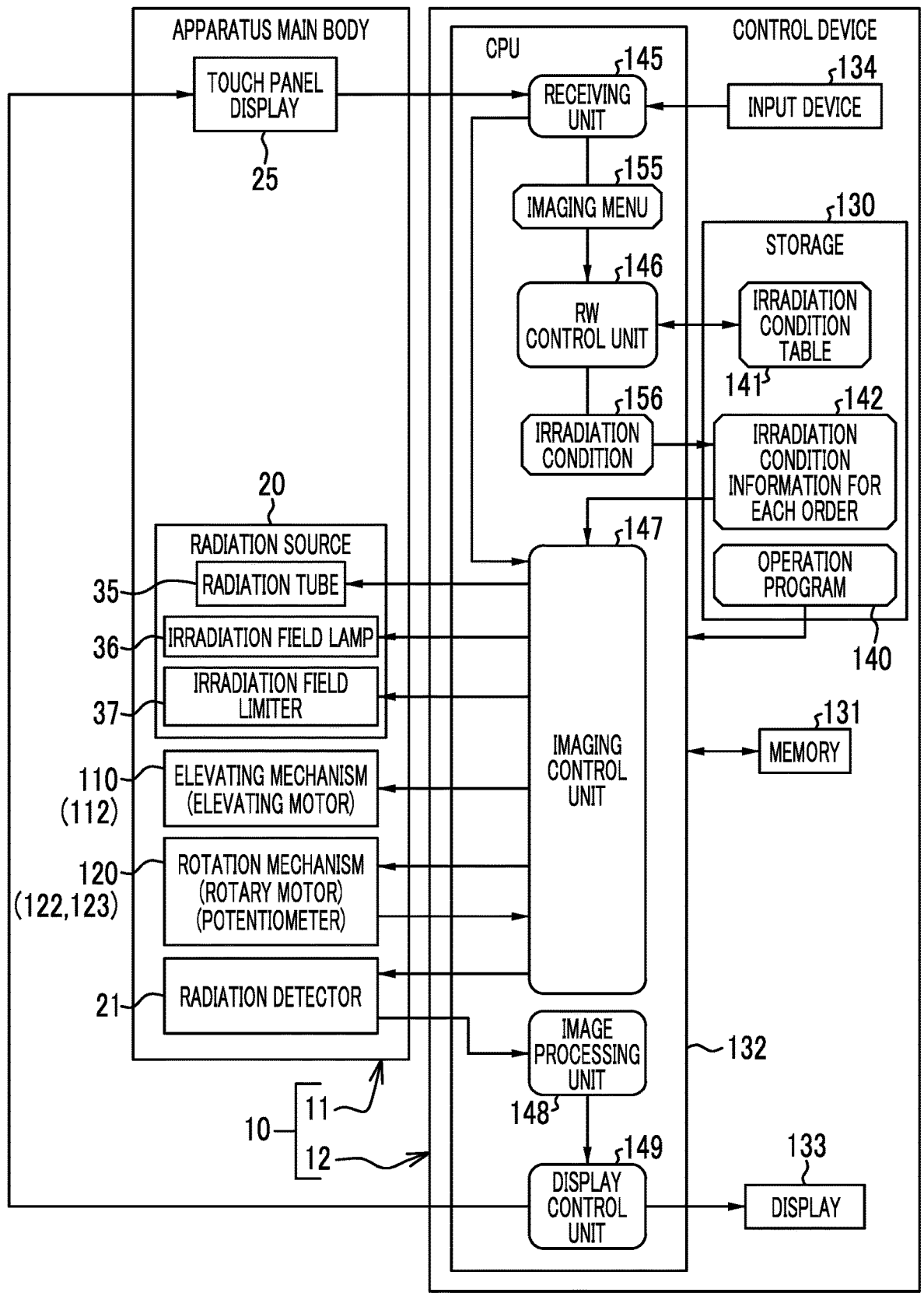
FIG. 18 is a block diagram illustrating a processing unit of a CPU of a control device.

For example, as illustrated in FIG. 18, a computer constituting the control device 12 comprises a storage 130, a memory 131, a central processing unit (CPU) 132, a display 133, an input device 134, and the like.

The storage 130 is a hard disk drive that is provided in the computer constituting the control device 12 or is connected to the computer through a cable or a network. Alternatively, the storage 130 is a disk array in which a plurality of hard disk drives are connected. The storage 130 stores, for example, a control program, such as an operating system, various application programs, and various kinds of data associated with these programs. In addition, a solid state drive may be used instead of the hard disk drive.

The memory 131 is a work memory that is used by the CPU 132 to perform processes. The CPU 132 loads the program stored in the storage 130 to the memory 131 and performs the process corresponding to the program. Therefore, the CPU 132 controls the overall operation of each unit of the computer. In addition, the memory 131 may be provided in the CPU 132.

The display 133 displays various screens. The various screens have operation functions by a graphical user interface (GUI). The computer constituting the control device 12 receives operation instructions input from the input device 134 through various screens. The input device 134 is, for example, a keyboard, a mouse, a touch panel, and a microphone for voice input.

An operation program 140 is stored in the storage 130. The operation program 140 is an application program for causing the computer to function as the control device 12. The storage 130 stores, for example, an irradiation condition table 141 and irradiation condition information 142 for each order, in addition to the operation program 140.

In a case in which the operation program 140 is started, the CPU 132 of the control device 12 functions as a receiving unit 145, a read and write (hereinafter, abbreviated to RW) control unit 146, an imaging control unit 147, an image processing unit 148, and a display control unit 149 in cooperation with, for example, the memory 131.

The receiving unit 145 receives various operation instructions input by the operator through the touch panel display 25 of the apparatus main body 11 and the input device 134. For example, the receiving unit 145 receives an imaging menu 155. The receiving unit 145 outputs the imaging menu 155 to the RW control unit 146.

The RW control unit 146 receives the imaging menu 155 from the receiving unit 145. The RW control unit 146 reads out irradiation conditions 156 of the radiation R which correspond to the received imaging menu 155 from the irradiation condition table 141. The RW control unit 146 writes the irradiation conditions 156 read from the irradiation condition table 141 to the irradiation condition information 142 for each order.

The imaging control unit 147 controls the operation of the radiation source 20 (the radiation tube 35, the irradiation field lamp 36, and the irradiation field limiter 37), the elevating mechanism 110 (elevating motor 112), the rotation mechanism 120 (the rotary motor 122 and the potentiometer 123), and the radiation detector 21. The imaging control unit 147 reads out the irradiation conditions 156 from the irradiation condition information 142 for each order. The imaging control unit 147 drives the irradiation field limiter 37 according to the irradiation conditions 156 to adjust the irradiation field. Further, the imaging control unit 147 drives the radiation tube 35 according to the irradiation conditions 156 such that the radiation R is emitted from the radiation tube 35. The imaging control unit 147 outputs a radiographic image (hereinafter, referred to as a projection image) which has been formed by the emission of the radiation R and detected by the radiation detector 21, from the radiation detector 21 to the image processing unit 148.

The image processing unit 148 acquires the projection image from the radiation detector 21. The image processing unit 148 performs various types of image processing on the projection image. Further, the image processing unit 148 performs a reconstruction process on a plurality of projection images subjected to the image processing to generate a tomographic image TI. The image processing unit 148 outputs the projection image or the tomographic image TI subjected to the image processing to the display control unit 149. In addition, the image processing unit 148 may perform a process of correcting the positional deviation of the pixels 104 caused by the thermal expansion and contraction of the sensor panel 42.

The display control unit 149 controls the display of various kinds of information on the touch panel display 25 and the display 133. The display control unit 149 receives the projection image or the tomographic image TI from the image processing unit 148. The display control unit 149 displays the projection image or the tomographic image TI on the touch panel display 25 and the display 133.

The imaging menu 155 includes, for example, imaging order identification data (ID) and an imaging procedure (see FIG. 19). The imaging order ID is identification information of the imaging order issued by a doctor who performs a medical examination using the tomographic image TI. The imaging procedure includes the posture of the subject S in a standing or sitting position, an imaging part, such as the head, the neck, or the spine, and the attributes of the subject S such as an adult male and an adult female.

The imaging order is transmitted from a radiology information system (RIS) (not illustrated) to the control device 12. The control device 12 displays a list of imaging orders on the display 133 under the control of the display control unit 149. The operator browses the list of imaging orders and checks the content of the list. Then, the control device 12 displays the imaging menu 155 corresponding to the imaging order on the display 133 such that it can be set. The operator operates the input device 134 to select the imaging menu 155 corresponding to the imaging order and to input the imaging menu 155.

For example, as illustrated in FIG. 19, the irradiation conditions 156 are registered in the irradiation condition table 141 for each imaging procedure. The irradiation conditions 156 include a tube voltage and a tube current applied to the radiation tube 35 and the irradiation time of the radiation R. In addition, the irradiation conditions 156 include the size of the irradiation field, which is not illustrated. The operator can finely adjust the irradiation conditions 156 by hand. Further, instead of the tube current and the irradiation time, a tube current-irradiation time product, that is, a so-called mAs value may be set as the irradiation condition 156.

A scout imaging position and a main imaging start position are also registered in the irradiation condition table 141 for each imaging procedure, which is not illustrated. The scout imaging position is a set of the height position and the rotation position of the frame 18 in scout imaging. The height position indicates the height of the frame 18 in a case in which the surface of the stage 13 is 0 cm. The rotation position is, for example, a position where the radiation source 20 faces the subject S, that is, a position of 0°. Alternatively, the rotation position may be a position of 90° where the radiation source 20 faces the right side surface of the subject S or a position of 270° where the radiation source 20 faces the left side surface of the subject S.

Here, the scout imaging is preliminary radiography that is performed to confirm the positioning of the subject S before the main imaging that captures a plurality of projection images at a predetermined angle to generate the tomographic image TI. In the scout imaging, the frame 18 is located at the height position and the rotation position registered in the irradiation condition table 141, and the radiation R is emitted with a lower dose than that in the main imaging to obtain one projection image. Hereinafter, the projection image obtained by the scout imaging is referred to as a scout image SI (see FIG. 20).

The main imaging start position is the rotation start position of the frame 18 in the main imaging. The main imaging start position is, for example, a position of 0°. Alternatively, the main imaging start position may be a position of 90°.

The irradiation conditions 156, the scout imaging position, and the main imaging start position are registered for each imaging order ID in the irradiation condition information 142 for each order, which is not illustrated. The imaging control unit 147 reads out the irradiation conditions 156, the scout imaging position, and the main imaging start position corresponding to the imaging order ID of the next imaging from the irradiation condition information 142 for each order and controls the operation of each unit on the basis of the read-out irradiation condition 156, scout imaging position, and main imaging start position.

In a case in which the subject S is guided into the apparatus main body 11, the frame 18 is moved to a retracted height position by the elevating mechanism 110 and is rotated to a position of 60° by the rotation mechanism 120 under the control of the imaging control unit 147. The retracted height position is set on the upper end side of the column 14. Specifically, the retracted height position is the position of the highest point in the elevation range of the frame 18. In this example, the position of the highest point in the elevation range of the frame 18 is the position of substantially the upper end of the column 14 and is the position where the second connection portion 114 of the connection member 17 comes into contact with the rear surface of the top plate 15. The position of 60° is a position where the entire radiation source 20 overlaps the column 14A. The operator guides the subject S into the apparatus main body 11 in this state through a space between the columns 14A and 14C as an entrance and positions the subject S.

After positioning the subject S in the apparatus main body 11, the operator stays at the installation position of the apparatus main body 11 and operates the touch panel display 25 to move the frame 18 to the height position registered in the irradiation condition table 141 and to rotate the frame 18 to the position of 0°. Then, the operator operates the touch panel display 25 to turn on the irradiation field lamp 36 and to irradiate the irradiation field with visible light, in order to confirm the irradiation field of the radiation R.

The operator visually recognizes the visible light from the irradiation field lamp 36 and determines whether the height position of the frame 18 and the positioning of the subject S are appropriate for imaging. In a case in which it is determined that the height position of the frame 18 and the positioning of the subject S are not appropriate for imaging, the operator operates the touch panel display 25 to adjust the height position of the frame 18 or to reposition the subject S. In a case in which it is determined that the height position of the frame 18 and the positioning of the subject S are appropriate for imaging, the operator operates the touch panel display 25 to turn off the irradiation field lamp 36.

Figure 20:
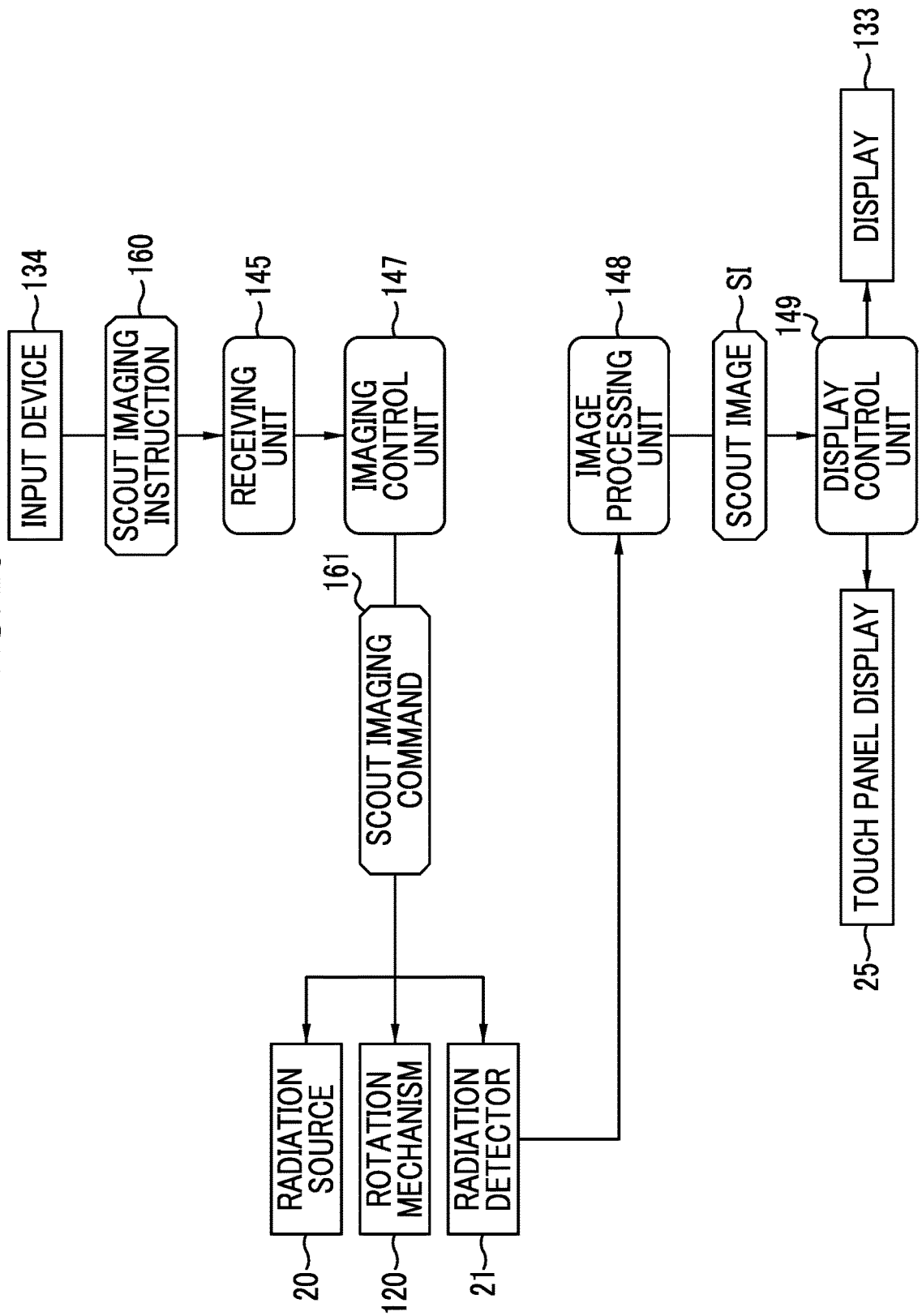
FIG. 20 is a diagram illustrating an outline of a process in a case in which a scout imaging instruction for performing scout imaging is input.

For example, as illustrated in FIG. 20, after confirming the irradiation field of the radiation R, the operator moves to the installation position of the control device 12 and operates the input device 134 to input a scout imaging instruction 160 for performing the scout imaging. The receiving unit 145 receives the scout imaging instruction 160 and outputs the instruction to the imaging control unit 147. The imaging control unit 147 outputs a scout imaging command 161 corresponding to the scout imaging instruction 160 to the radiation source 20, the radiation detector 21, and the rotation mechanism 120.

The content of the scout imaging command 161 is that the height position at the time of confirming the irradiation field of the radiation R is maintained and the frame 18 is rotated to the rotation position which is the scout imaging position registered in the irradiation condition table 141. Further, the content of the scout imaging command 161 is that the scout imaging is performed at the height position at the time of confirming the irradiation field of the radiation R and the rotation position which is the scout imaging position registered in the irradiation condition table 141. The rotation mechanism 120 drives the rotary motor 122 to rotate the rotation belt 121, thereby rotating the frame 18 to the rotation position which is the scout imaging position registered in the irradiation condition table 141.

The radiation source 20 drives the radiation tube 35 to irradiate the subject S with the radiation R for scout imaging. The radiation detector 21 detects the radiation R transmitted through the subject S to obtain the projection image. The radiation detector 21 outputs the projection image to the image processing unit 148.

The image processing unit 148 performs various types of image processing on the projection image from the radiation detector 21 to obtain the scout image SI. The image processing unit 148 outputs the scout image SI to the display control unit 149. The display control unit 149 displays the scout image SI on the touch panel display 25 and the display 133.

The operator browses the scout image SI on the display 133 and determines whether the height position of the frame 18 and the positioning of the subject S are appropriate for imaging. In a case in which it is determined that the height position of the frame 18 and the positioning of the subject S are not appropriate for imaging from the scout image SI, the operator returns to the installation position of the apparatus main body 11 and turns on the irradiation field lamp 36 again to adjust the height position of the frame 18 or to reposition the subject S.

Figure 21:
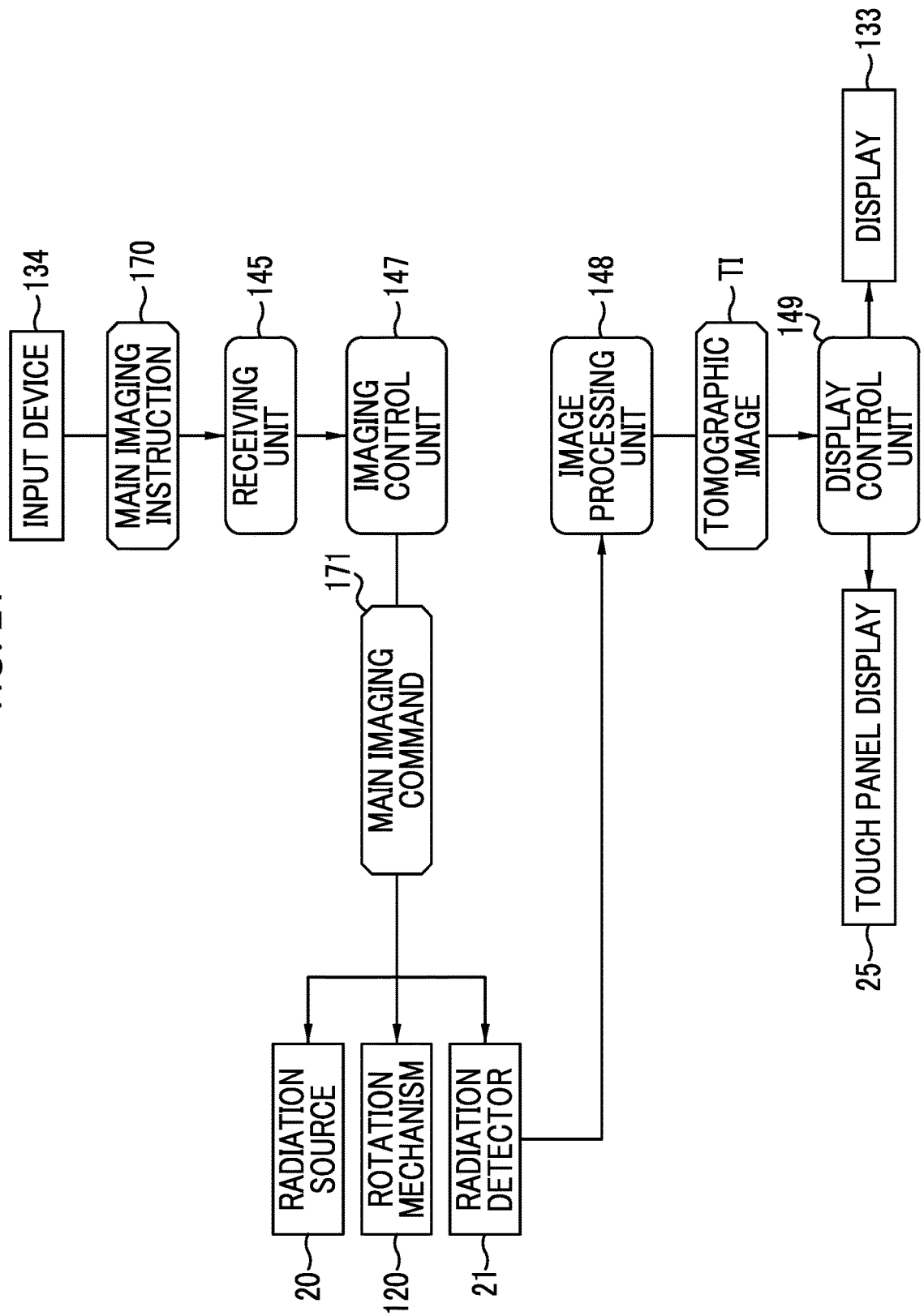
FIG. 21 is a diagram illustrating an outline of a process in a case in which a main imaging instruction for performing main imaging is input.

For example, as illustrated in FIG. 21, in a case in which it is determined that the height position of the frame 18 and the positioning of the subject S are appropriate for imaging from the scout image SI, the operator operates the input device 134 to input a main imaging instruction 170 for performing the main imaging. The receiving unit 145 receives the main imaging instruction 170 and outputs the instruction to the imaging control unit 147. The imaging control unit 147 outputs a main imaging command 171 corresponding to the main imaging instruction 170 to the radiation source 20, the radiation detector 21, and the rotation mechanism 120.

The content of the main imaging command 171 is that the height position at the time of the end of the scout imaging is maintained and the frame 18 is rotated to the main imaging start position and is then rotated to a main imaging end position in the counterclockwise direction CCW. Further, the content of the main imaging command 171 is that the main imaging is performed while the frame 18 is rotated from the main imaging start position to the main imaging end position. The rotation mechanism 120 drives the rotary motor 122 to rotate the rotation belt 121 such that the frame 18 is first rotated to the main imaging start position. Then, the rotation mechanism 120 rotates the frame 18 to the main imaging end position in the counterclockwise direction CCW. In this example, the main imaging end position is a position that is rotated by 225° in the counterclockwise direction CCW from the main imaging start position. In a case in which the main imaging start position is a position of 0°, the main imaging end position is a position of 135° that is rotated by 225° in the counterclockwise direction CCW from the position of 0°. Further, in a case in which the main imaging start position is 90°, the main imaging end position is a position of 225°. In a case in which the main imaging start position is 180°, the main imaging end position is a position of 315°.

The radiation source 20 drives the radiation tube 35 at a predetermined angle to irradiate the subject S with the radiation R for main imaging according to the irradiation conditions 156 at a predetermined angle. The radiation detector 21 detects the radiation R transmitted through the subject S at a predetermined angle to obtain a plurality of projection images. The radiation detector 21 sequentially outputs the plurality of projection images to the image processing unit 148.

The image processing unit 148 performs a reconstruction process on the plurality of projection images from the radiation detector 21 to obtain the tomographic image TI. The image processing unit 148 outputs the tomographic image TI to the display control unit 149. The display control unit 149 displays the tomographic image TI on the touch panel display 25 and the display 133.

The operator browses the tomographic image TI on the display 133 and determines whether or not the tomographic image TI needs to be re-captured. In a case in which it is determined that the tomographic image TI needs to be re-captured, the operator operates the input device 134 to re-input the main imaging instruction 170.

In a case in which it is determined that the tomographic image TI does not need to be re-captured, the operator operates the input device 134 to return the frame 18 to the retracted height position. Further, the frame 18 is rotated in the clockwise direction CW from the imaging end position and is returned to the position of 60°. Then, the operator retracts the subject S from the inside of the apparatus main body 11.

Figure 22:
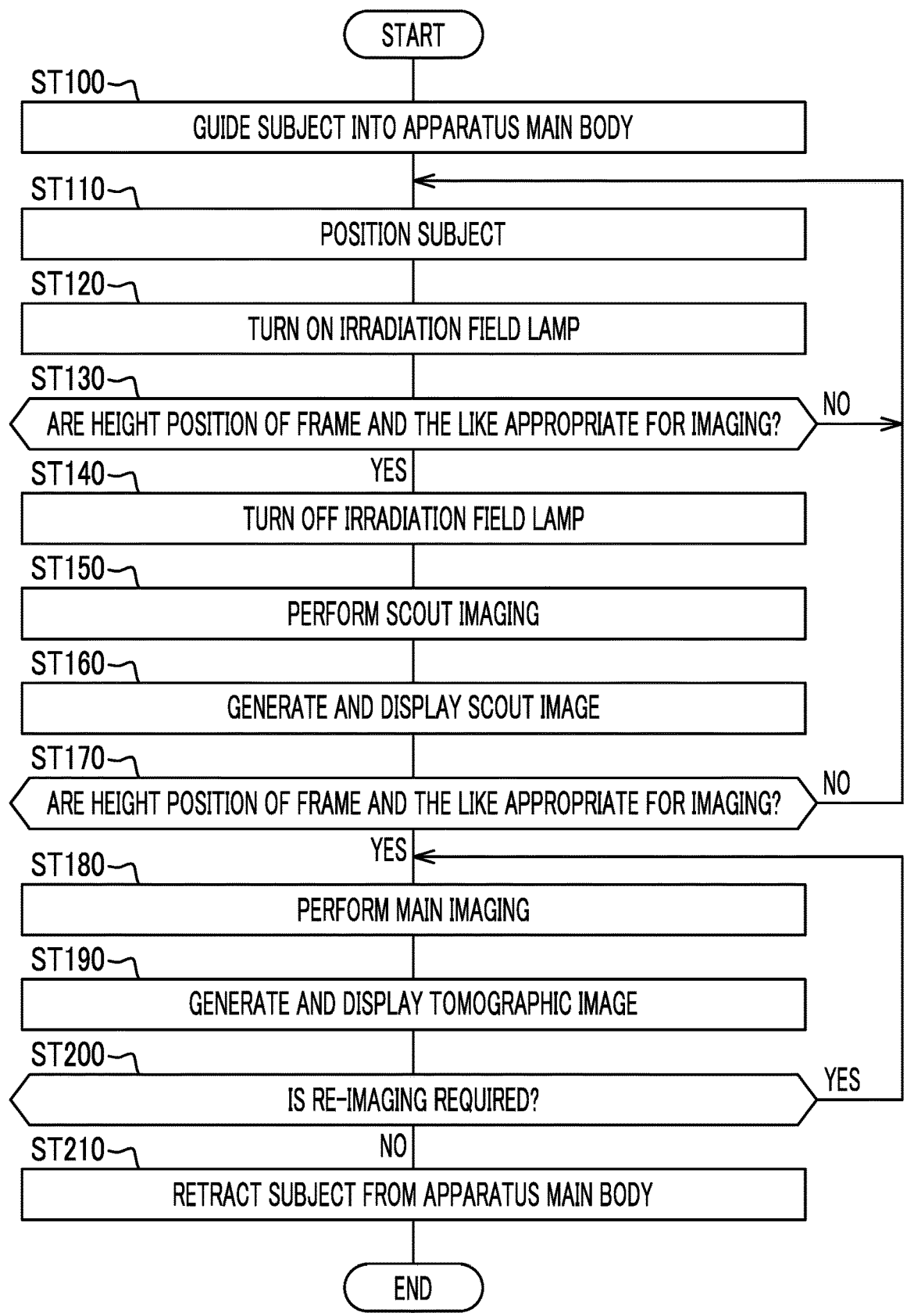
FIG. 22 is a flowchart illustrating a procedure of capturing a tomographic image by the CT apparatus.

Next, the operation of the above-mentioned configuration will be described with reference to a flowchart illustrated in FIG. 22. In a case in which the operation program 140 is started, the CPU 132 of the control device 12 functions as the receiving unit 145, the RW control unit 146, the imaging control unit 147, the image processing unit 148, and the display control unit 149 as illustrated in FIG. 18.

First, in a state in which the frame 18 is moved to the retracted height position and is rotated to the position of 60°, the operator guides the subject S into the apparatus main body 11 (Step ST100). Then, the operator positions the subject S (Step ST110).

After positioning the subject S, the operator inputs an instruction to turn on the irradiation field lamp 36 through the touch panel display 25. Then, the elevating mechanism 110 is operated to move the frame 18 to the height position registered in the irradiation condition table 141. Further, the rotation mechanism 120 is operated to rotate the frame 18 to the position of 0°. Further, after the irradiation field limiter 37 is driven and adjusted to the irradiation field corresponding to the irradiation conditions 156, the irradiation field lamp 36 is turned on, and the irradiation field is irradiated with visible light (Step ST120).

The operator determines whether or not the height position of the frame 18 and the positioning of the subject S are appropriate for imaging with reference to the visible light from the irradiation field lamp 36 (Step ST130). In a case in which the height position of the frame 18 and the positioning of the subject S are not appropriate for imaging (NO in Step ST130), the operator adjusts the height position of the frame 18 or repositions the subject S. In a case in which the height position of the frame 18 and the positioning of the subject S are appropriate for imaging (YES in Step ST130), the operator inputs an instruction to turn off the irradiation field lamp 36 through the touch panel display 25, and the irradiation field lamp 36 is turned off (Step ST140).

As illustrated in FIG. 20, after confirming the irradiation field of the radiation R, the operator inputs the scout imaging instruction 160 through the input device 134. The receiving unit 145 receives the scout imaging instruction 160. Then, the scout imaging command 161 is output from the imaging control unit 147 to, for example, the radiation source 20.

The rotation mechanism 120 is operated by the scout imaging command 161 to rotate the frame 18 to the rotation position registered in the irradiation condition table 141. Further, the radiation tube 35 irradiates the subject S with the radiation R for scout imaging, and the radiation detector 21 detects the radiation R transmitted through the subject S to obtain the projection image (Step ST150).

The image processing unit 148 performs various types of image processing on the projection image obtained by the radiation detector 21 to obtain the scout image SI. The scout image SI is displayed on the touch panel display 25 and the display 133 under the control of the display control unit 149 (Step ST160).

The operator determines whether or not the height position of the frame 18 and the positioning of the subject S are appropriate for imaging again with reference to the scout image SI (Step ST170). In a case in which the height position of the frame 18 and the positioning of the subject S are not appropriate for imaging (NO in Step ST170), the operator adjusts the height position of the frame 18 or repositions the subject S.

In a case in which the height position of the frame 18 and the positioning of the subject S are appropriate for imaging (YES in Step ST170), the operator inputs the main imaging instruction 170 through the input device 134 as illustrated in FIG. 21. The receiving unit 145 receives the main imaging instruction 170. Then, the main imaging command 171 is output from the imaging control unit 147 to, for example, the radiation source 20.

The rotation mechanism 120 is operated in response to the main imaging command 171 to first rotate the frame 18 to the main imaging start position. Then, the frame 18 is rotated to the main imaging end position in the counterclockwise direction CCW. During that time, the radiation tube 35 irradiates the subject S with the radiation R for main imaging at a predetermined angle, and the radiation detector 21 detects the radiation R transmitted through the subject S whenever the subject S is irradiated to obtain a plurality of projection images (Step ST180).

The image processing unit 148 performs the reconstruction process on the plurality of projection images obtained by the radiation detector 21 to obtain the tomographic image TI. The tomographic image TI is displayed on the touch panel display 25 and the display 133 under the control of the display control unit 149 (Step ST190).

The operator determines whether or not the tomographic image TI needs to be re-captured (Step ST200). In a case in which the operator determines that the tomographic image TI needs to be re-captured (YES in Step ST200), the operator inputs the main imaging instruction 170 through the input device 134, and the process returns to Step ST180.

In a case in which the operator determines that the tomographic image TI does not need to be re-captured (NO in Step ST200), the elevating mechanism 110 is operated in response to an instruction from the operator through the input device 134 to return the frame 18 to the retracted height position. Further, the rotation mechanism 120 is operated to return the frame 18 from the imaging end position to the position of 60° in the clockwise direction CW. After the frame 18 is returned to the retracted height position and the position of 60°, the operator retracts the subject S from the apparatus main body 11 (Step ST210). The series of Steps ST100 to ST210 is repeated in a case in which there is the next imaging order.

As illustrated in FIG. 8 and the like, the radiation detector 21 comprises the sensor panel unit 41, the support table 52 to which the sensor panel unit 41 is attached, the fixing members 51, and the fixing members 59. The sensor panel unit 41 includes two sensor panels 42, that is, the sensor panels 42A and 42B. The sensor panel 42 has the pixels 104 that sense visible light converted from the radiation R and generate charge. The sensor panel unit 41 has a configuration in which the end portion 50A of the sensor panel 42A and the end portion 50B of the sensor panel 42B are arranged so as to overlap each other in the thickness direction. The fixing members 51 fix the sensor panel 42A and the sensor panel 42B in the overlap region 65 in which the end portion 50A and the end portion 50B overlap each other. The fixing members 59 fix the sensor panel unit 41 and the support table 52 in the overlap region 65. The fixing member 59 at least partially overlaps the fixing member 51 in the overlap region 65 in a plan view of the sensor panel unit 41 in the thickness direction.

Therefore, the fixed positions of the sensor panel 42A and the sensor panel 42B by the fixing members 51 and the fixed positions of the sensor panel unit 41 and the support table 52 by the fixing members 59 fall in the overlap region 65. Therefore, the sensor panels 42A and 42B are thermally expanded or contracted on the basis of the overlap region 65. That is, the sensor panels 42A and 42B are thermally expanded or contracted substantially in the same way. The fixing members 51 and 59 preserve the positional relationship between the sensor panel 42A and the sensor panel 42B and between the sensor panel unit 41 and the support table 52. Therefore, in a case in which the sensor panels 42A and 42B are thermally expanded or contracted and then returned to the original state, there is a high possibility that the sensor panels 42A and 42B will be returned to their original positions. Therefore, it is possible to improve the reproducibility of the positions of the two sensor panels 42A and 42B in which the end portions 50A and 50B are arranged so as to overlap each other.

The fixing members 51 partially fix the sensor panel 42A and the sensor panel 42B, and the fixing members 59 partially fix the sensor panel unit 41 and the support table 52. In a case in which the sensor panel 42A and the sensor panel 42B are fixed by the fixing members 51 over the entire overlap region 65 and the sensor panel unit 41 and the support table 52 are fixed by the fixing members 59 over the entire overlap region 65, there is a possibility that wrinkles will occur in the sensor panels 42A and 42B due to thermal expansion and contraction. However, since the sensor panels 42A and 42B are partially fixed, it is possible to significantly reduce the possibility.

As illustrated in FIG. 10, the imaging region 61A of the sensor panel 42A and the imaging region 61B of the sensor panel 42B overlap each other in the overlap region 65 in a plan view of the sensor panel unit 41 in the thickness direction. Therefore, it is possible to prevent a region in which it is difficult to detect the projection image from being generated in the overlap region 65.

Further, the fixing member 51 is disposed at a position that does not protrude from the overlap imaging region 66, in which the imaging region 61A and the imaging region 61B overlap each other, to the imaging region 61B. In the overlap region 65, the position that protrudes from the overlap imaging region 66 to the imaging region 61B corresponds to the non-imaging region 62A of the sensor panel 42A. Therefore, the projection image at the position that protrudes from the overlap imaging region 66 to the imaging region 61B can be detected only by the sensor panel 42B. Therefore, in a case in which the fixing member 51 is disposed at a position that does not protrude from the overlap imaging region 66 to the imaging region 61B, the fixing member 51 is prevented from being reflected in a portion that can be detected only by the sensor panel 42B. As a result, it is possible to suppress the deterioration of the quality of the tomographic image TI.

The spacer 55 that is disposed between the sensor panel 42A and the support table 52 and has a thickness corresponding to the distance between the sensor panel 42A and the support table 52 is provided. Therefore, the sensor panel 42A can be attached in a shape that follows the attachment surface 53 of the support table 52.

The sensor panel unit 41 includes two sensor panels 42A and 42B. Therefore, it is possible to provide the overlap region 65, which causes the deterioration of the quality of the tomographic image TI, at a minimum of one position, and thus to suppress the deterioration of the quality of the tomographic image TI. In addition, the number of sensor panels 42 is not limited to two and may be three or more. In a case in which the number of sensor panels is increased, it is possible to image a wider range of the subject S at one time.

The support table 52 has the attachment surface 53 that has an arc surface shape toward the opposite side of the radiation source 20, and the sensor panel unit 41 is attached to the attachment surface 53 following the arc surface shape. For example, in a case in which the sensor panel 41 has a planar shape, as represented by a broken line in FIG. 23, the irradiation dose of the radiation R in an end portion is lower than that in a central portion of the sensor panel unit 41. As a result, a scan field of view (sFOV) 1, which is an imaging range that can be reconstructed as the tomographic image TI, is reduced. On the other hand, in a case in which the sensor panel unit 41 has an arc surface shape, the entire sensor panel unit 41 is irradiated with substantially the same amount of radiation R. Therefore, a scan field of view sFOV2 can be larger than the scan field of view sFOV1 (sFOV2>SFOV1). For example, while sFOV1 is 384 mm, sFOV2 is 406 mm. Therefore, the sensor panel unit 41 having an arc surface shape makes it possible to image a wider range of the subject S at once.

In addition, in some CT apparatuses according to the related art, a flat sensor panel unit 41 is moved in a plane direction to obtain sFOV1. However, this CT apparatus has disadvantages that a moving mechanism for moving the sensor panel unit 41 in the plane direction is required, which results in an increase in the size of the apparatus, and it takes a long time to perform imaging. In contrast, the CT apparatus 10 according to this example does not require the moving mechanism and does not take a long time for imaging.

As illustrated in FIG. 10, the tangent line TGA between the sensor panel 42A and the fixing member 51 is parallel to the tangent line TGB between the sensor panel 42B and the fixing member 59. Therefore, it is possible to make the degrees of thermal expansion and contraction of the sensor panels 42A and 42B closer to each other. In addition, it is possible to further improve the reproducibility of the positions of the sensor panels 42A and 42B.

As illustrated in FIG. 13, in the sensor panel 42, the pixels 104 including TFTs are two-dimensionally arranged. The sensor panel 42 using the TFTs can have a larger area and a higher resolution than other imaging sensors such as complementary metal oxide semiconductor (CMOS) solid-state imaging elements. Therefore, it is possible to image a wider range of the subject S at one time and to obtain a high-quality tomographic image TI. In addition, the imaging sensor is not limited to the sensor panel 42 and may be a CMOS solid-state imaging element.

As illustrated in FIG. 13, the thickness TH of the substrate 100 of the sensor panel 42 is equal to or less than 100 μm. Therefore, wrinkles caused by thermal expansion and contraction are likely to occur, as compared to a case in which the thickness TH is greater than 100 μm. In addition, the end portion of the sensor panel 42 is likely to be lifted from the support table 52. Therefore, it is possible to further exert the effect of the technology of the present disclosure that it is possible to improve the reproducibility of the position of the sensor panel 42.

As illustrated in FIG. 13, the support table 52 is made of metal, and the substrate 100 of the sensor panel 42 is made of a resin. Therefore, the difference between the thermal expansion coefficients of the sensor panel 42 and the support table 52 is larger, and wrinkles caused by thermal expansion and contraction are likely to occur. In addition, the end portion of the sensor panel 42 is likely to be lifted from the support table 52. Therefore, it is possible to further exert the effect of the technology of the present disclosure that it is possible to improve the reproducibility of the position of the sensor panel 42.

As illustrated in FIG. 12 and the like, the contact members 70 to 72 that come into contact with the second surface 60 of the sensor panel 42 which is opposite to the first surface 54 and suppress the lifting of the sensor panel 42 from the support table 52 are provided. Therefore, it is possible to significantly reduce the possibility that the end portion of the sensor panel 42 will be lifted from the support table 52 due to the difference between the thermal expansion coefficients of the sensor panel 42 and the support table 52.

As illustrated in FIG. 13, the contact members 70 to 72 bias the sensor panel 42 to the attachment surface 53. Therefore, it is possible to further reduce the possibility that the end portion of the sensor panel 42 will be lifted from the support table 52.

As illustrated in FIG. 15, the contact members 70 to 72 are deformed according to the thermal expansion and contraction of the sensor panel 42 in the plane direction PD. The contact members 70 to 72 are deformed in this way to allow the thermal expansion and thermal contraction of the sensor panel 42 in the plane direction PD, which makes it possible to further reduce the possibility that wrinkles caused by thermal expansion and thermal contraction will occur in the sensor panel 42.

In the contact members 70 to 72, the second length L_PD along the plane direction PD is smaller than the first length L_ND along the normal direction ND. Therefore, as compared to a case in which the length L_ND is equal to or less than the length L_PD, the contact members 70 to 72 are more likely to be deformed according to the thermal expansion and contraction of the sensor panel 42 in the plane direction PD.

As illustrated in FIG. 13, in the contact members 70 and 71, the contact surfaces 73 and 74 with the second surface 60 have a shape following the arc surface shape. Therefore, the contact condition of the contact members 70 and 71 with the second surface 60 does not change depending on the location, and it is possible to prevent the sensor panel 42 from being subjected to extra stress.

The holding members 79 to 81 that hold the contact members 70 to 72 and have a higher rigidity than the contact members 70 to 72 are provided. Therefore, it is possible to stably maintain the biasing force for biasing the sensor panel 42 to the attachment surface 53.

As illustrated in FIG. 14, the contact members 70 to 72 come into contact with the non-imaging region 62. Therefore, the contact members 70 to 72 are not reflected in the projection image and thus the tomographic image TI, which makes it possible to prevent the deterioration of the quality of the tomographic image TI.

As illustrated in FIG. 14, the contact members include the contact members 70A and 71B that are disposed on the sides 44A and 43B to which the reading circuit boards 46A and 46B are attached and the contact members 71A and 70B that are disposed on the sides 43A and 44B which face the sides 44A and 43B and to which the reading circuit boards 46A and 46B are not attached. In addition, the contact members 70A and 71B have a higher biasing force than the contact members 71A and 70B. The end portions on the sides 44A and 43B have a strong repulsive force since the reading circuit boards 46A and 46B are attached to the end portions and are likely to be lifted. However, the biasing force of the contact members 70A and 71B can be increased to more firmly suppress the lifting of the end portions on the sides 44A and 43B.

The radiation shielding members 97 and 98 that shield the radiation R to protect the reading circuit board 46 and the switching circuit board 48 are attached to the contact members 70 and 72. Therefore, it is possible to prevent the performance of the reading circuit board 46 and the switching circuit board 48 from being deteriorated by the radiation R.

The CT apparatus 10 comprises the radiation detector 21 and the radiation source 20 that emits the radiation R. Since the reproducibility of the position of the sensor panel 42 in the radiation detector 21 is high, it is possible to obtain the tomographic image TI with little deterioration in image quality as a result.

Figure 24:
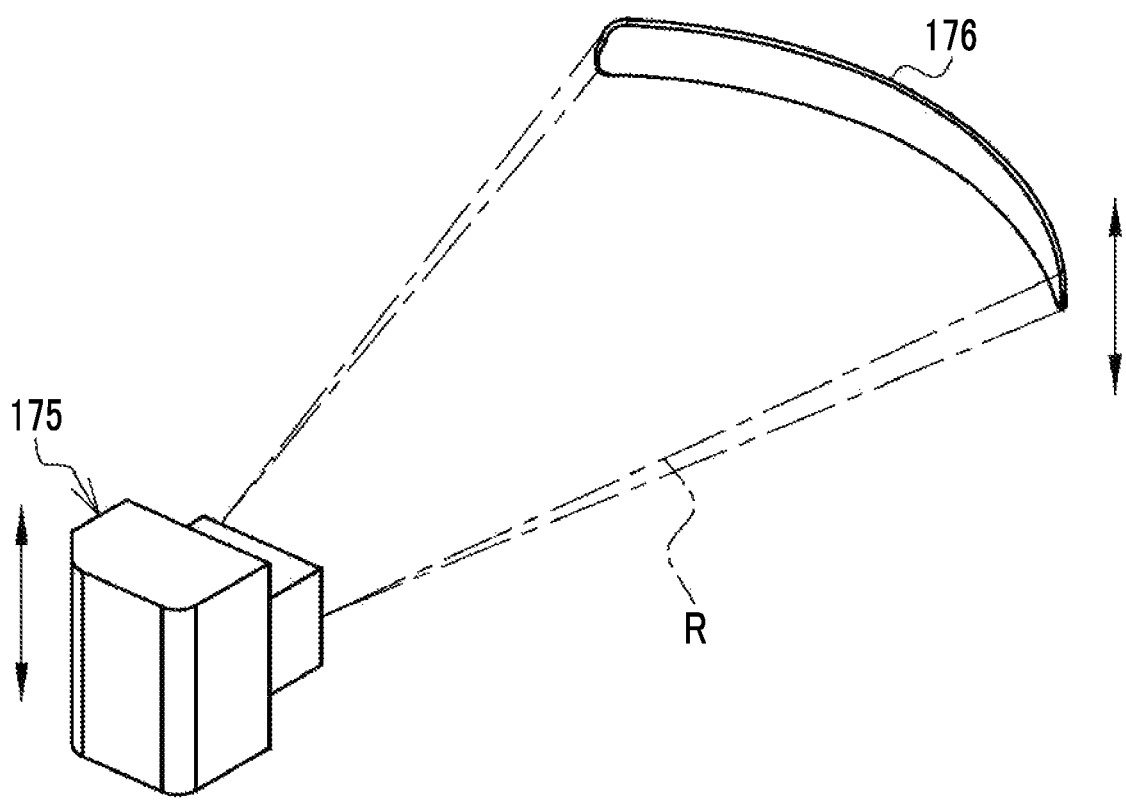
FIG. 24 is a diagram illustrating a radiation source and a radiation detector of a CT apparatus according to the related art.

For example, as illustrated in FIG. 24, the typical CT apparatus according to the related art described in JP2003-339688A and the like has a configuration in which a radiation source 175 emits fan-shaped radiation R to scan the subject in the height direction (the body axis direction of the subject S) and a radiation detector 176 having an imaging sensor unit in which a plurality of strip-shaped imaging sensors, such as CMOS solid-state imaging elements, are arranged detects the radiation R while being moved. The CMOS solid-state imaging element has a strip shape in which the length in the height direction is small and has a small area. Therefore, the CMOS solid-state imaging element is more easily held stably than the sensor panel 42 having a relatively large area. However, it takes a long imaging time to perform scanning with the radiation R. Further, in a case in which three or more imaging sensors are arranged to form a radiation detector having a large area as a whole in order to shorten the imaging time as in JP2003-339688A, there is a concern that the quality of the tomographic image TI will deteriorate due to the joints of each imaging sensor.

In contrast, as illustrated in, for example, FIGS. 6 and 7, the CT apparatus 10 uses the sensor panel 42 having a relatively large area in order to eliminate the need for scanning with the radiation R and to minimize the deterioration of the quality of the tomographic image TI caused by the joint. In addition, a fixing method is devised to improve the reproducibility of the position of the sensor panel 42 which has difficulty in improving the reproducibility of the position since it has a large area. Therefore, it is possible to shorten the imaging time as compared to the CT apparatus according to the related art which performs scanning with the radiation R. In addition, it is possible to suppress the deterioration of the quality of the tomographic image TI as compared to the CT apparatus according to the related art in which three or more imaging sensors are arranged.

Figure 23:
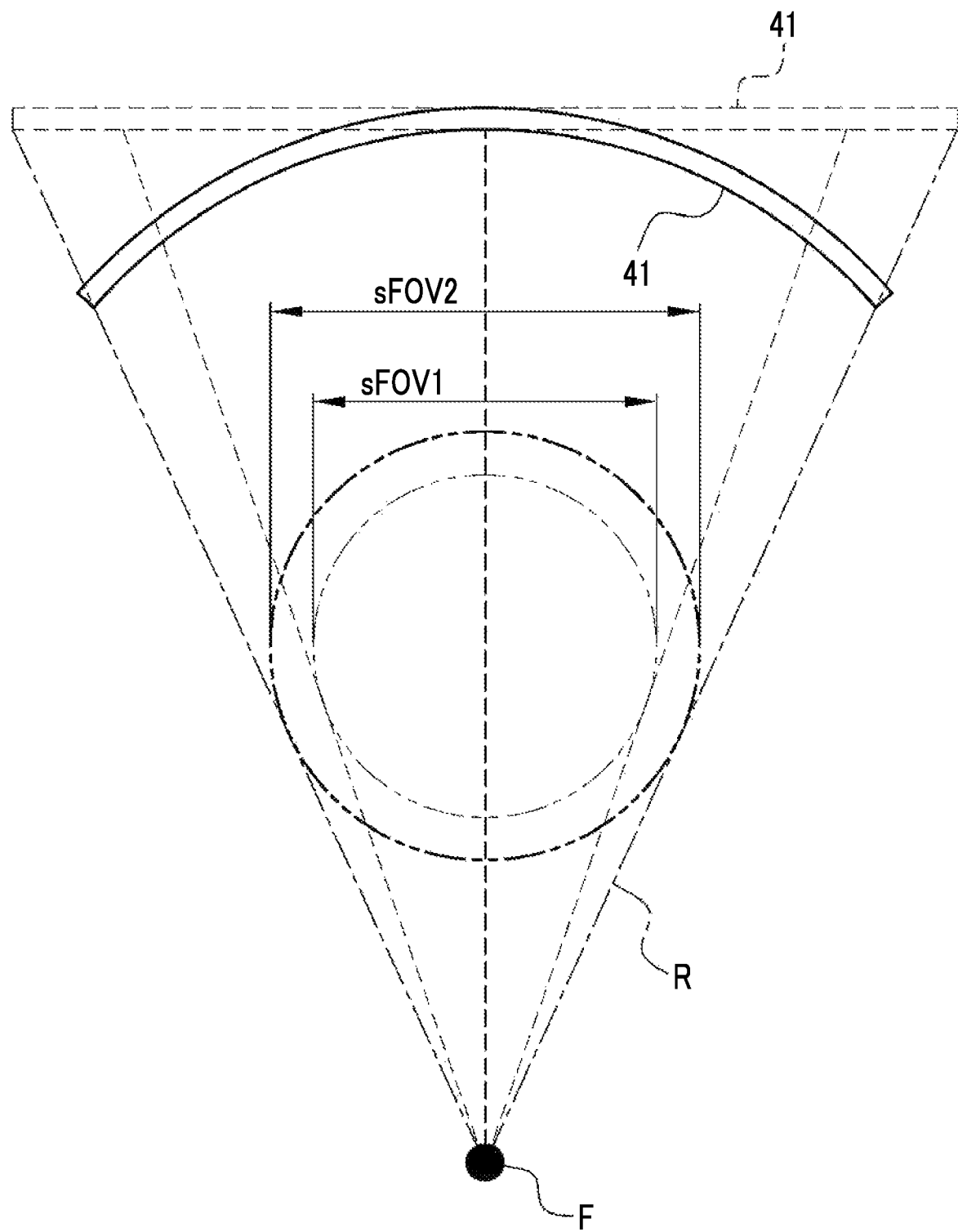
FIG. 23 is a diagram illustrating a scan field of view in a case in which the sensor panel has an arc surface shape and in a case in which the sensor panel has a planar shape.

The CT apparatus 10 comprises the annular frame 18 to which the radiation source 20 and the radiation detector 21 are attached and the rotation mechanism 120. The subject S is positioned in the cavity 19 of the frame 18. The rotation mechanism 120 rotates the frame 18 around the subject S in order to capture the projection images of the subject S at different angles. The support table 52 has the attachment surface 53 with an arc surface shape following the annular frame 18, and the sensor panel unit 41 is attached to the attachment surface 53 following the arc surface shape. As illustrated in FIG. 23, the sensor panel unit 41 having an arc surface shape makes it possible to image a wider range of the subject S at one time.

In this example, the radiography apparatus is the CT apparatus 10 that obtains the tomographic image TI of the subject S on the basis of the projection images captured at different angles. In a case in which the reproducibility of the position of the sensor panel 42 is low, a large deviation may occur in the projection images captured at different angles. As a result, there is a concern that the quality of the tomographic image TI will deteriorate significantly. However, in this embodiment, since the reproducibility of the position of the sensor panel 42 is high, it is possible to reduce the concern that the quality of the tomographic image TI will deteriorate.

As illustrated in FIG. 6, the radiation source 20 emits the radiation R with a quadrangular pyramid shape. Therefore, it is possible to complete imaging in a short time as compared to a case in which the radiation source emits the radiation R with a fan shape to perform scanning in the height direction. In addition, the radiation R having a conical shape instead of the quadrangular pyramid shape may be emitted.

As illustrated in FIGS. 1 and 5, the subject S is positioned in the cavity 19 in either the standing posture or the sitting posture. Therefore, it is possible to meet the doctor's desire to observe soft tissues, such as the lungs, in a natural state in which gravity is applied or to observe joints, such as hip joints, in a state in which gravity is applied and a load is applied.

Figure 25:
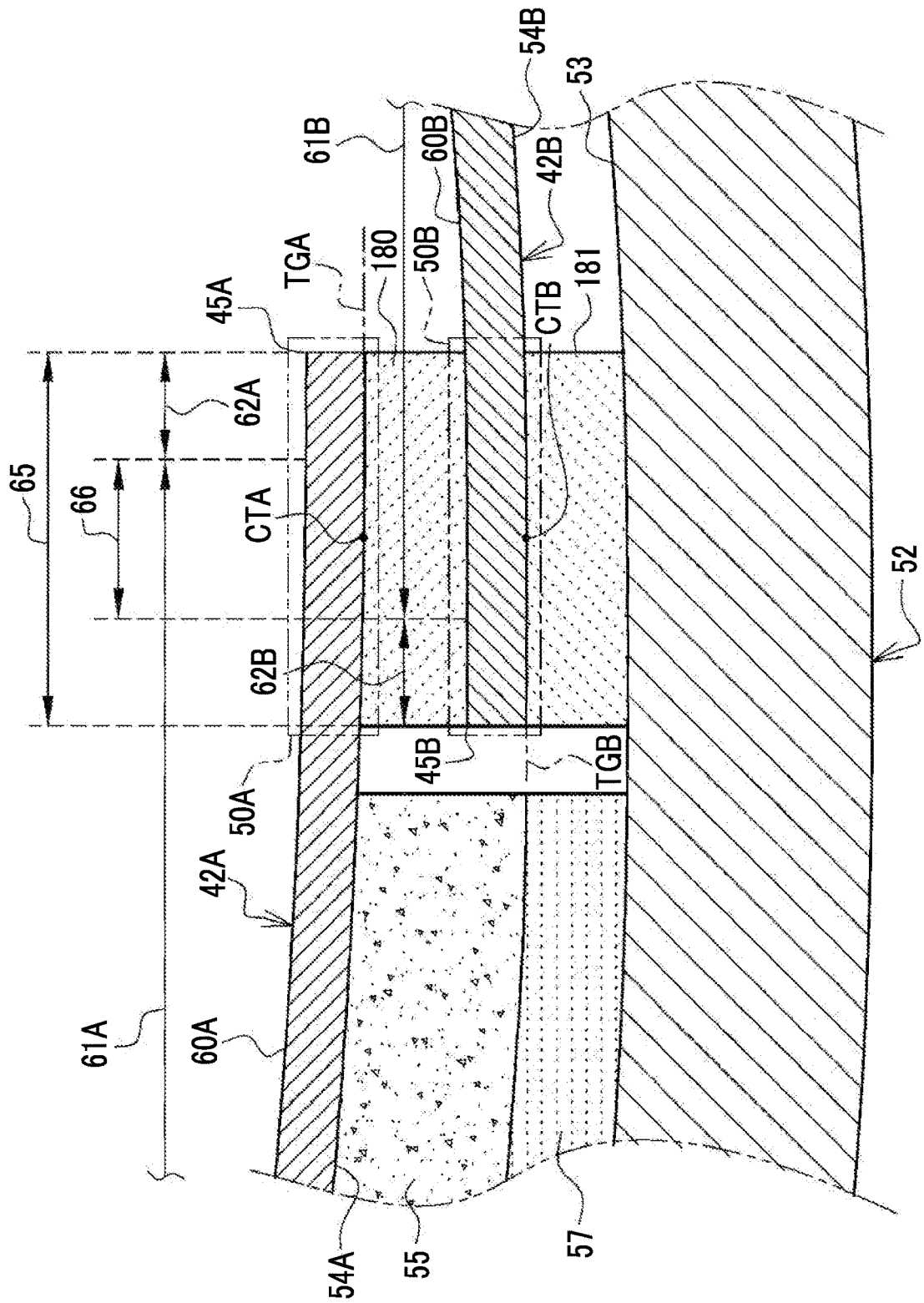
FIG. 25 is a diagram illustrating an example in which two sensor panels are fixed by fixing members having the same width as the overlap region.

In the above-mentioned example, the fixing member 51 is disposed at a position that does not protrude from the overlap imaging region 66 to the imaging region 61B. However, the present disclosure is not limited thereto. For example, as illustrated in FIG. 25, the sensor panel 42A and the sensor panel 42B may be fixed by a fixing member 180 having the same width as the overlap region 65. In this case, a fixing member 181 that fixes the sensor panel unit 41 and the support table 52 also has the same width as the overlap region 65. In addition, the term "same" in the "same width" indicates "same" including an error (for example, an error of about 1% to 10%) that is generally allowed in the technical field to which the technology of the present disclosure belongs and does not depart from the gist of the technology of the present disclosure in addition to exact "same" as described in paragraph.

The fixing member 180 is an example of the "first fixing member" according to the technology of the present disclosure, and the fixing member 181 is an example of the "second fixing member" according to the technology of the present disclosure. With this configuration, the quality of the tomographic image TI is sacrificed to some extent, but it is possible to ensure a wider fixing region of the sensor panel 42A and the sensor panel 42B and to more firmly fix the sensor panel 42A and the sensor panel 42B, as compared to a case in which the fixing member 51 is disposed at a position that does not protrude from the overlap imaging region 66 to the imaging region 61B.

Figure 26:
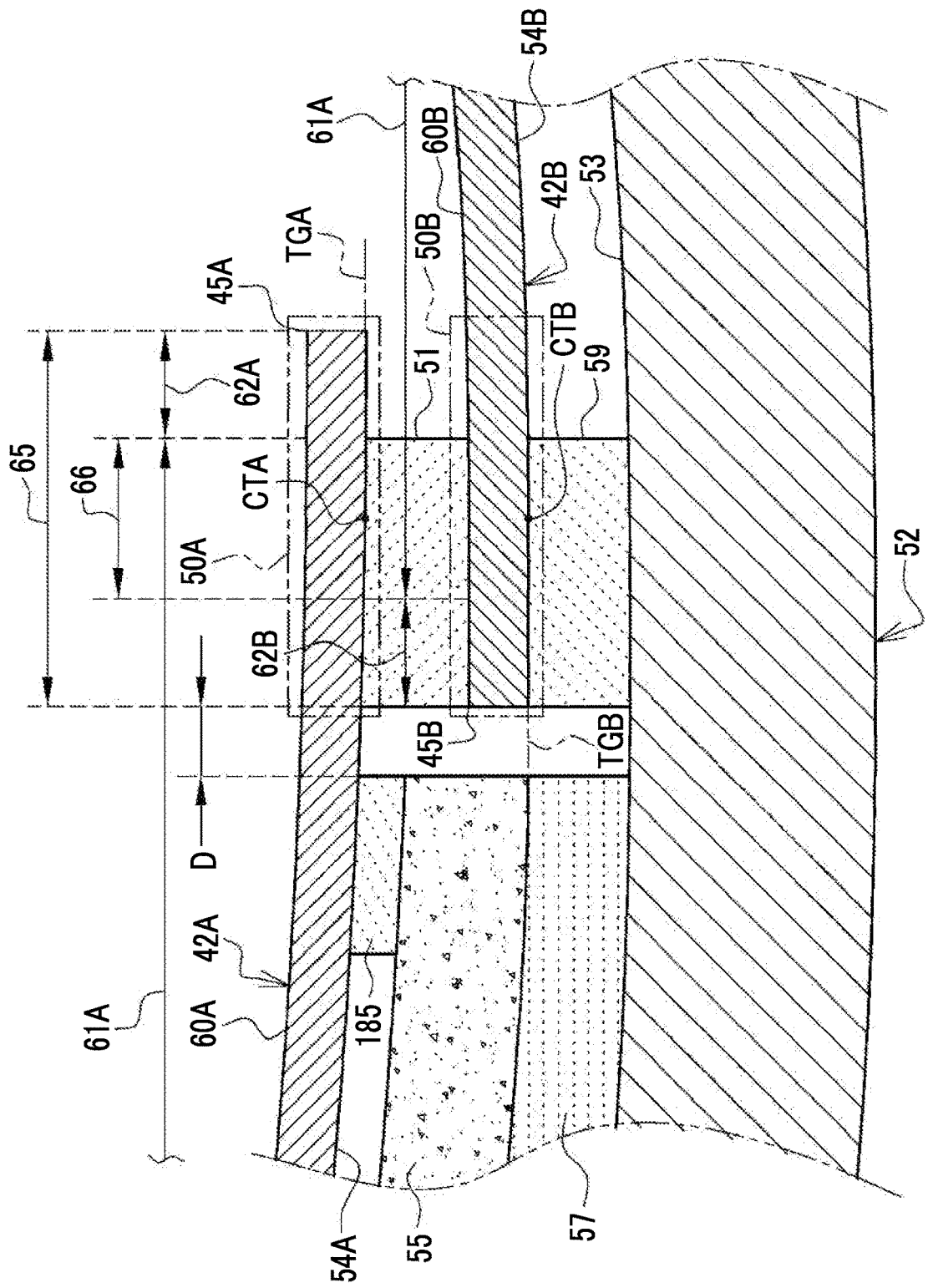
FIG. 26 is a diagram illustrating an example in which the sensor panel and the spacer are fixed by the fixing member.

Further, in the case of the above-mentioned example in which the fixing member 51 is disposed at the position that does not protrude from the overlap imaging region 66 to the imaging region 61B, for example, as illustrated in FIG. 26, the sensor panel 42A and the spacer 55 may be fixed by a fixing member 185 at a position that is adjacent to the fixing member 51. The position adjacent to the fixing member 51 means a position where the distance D from the fixing member 51 is, for example, within 1 mm. Therefore, the fixing member 51 and the fixing member 185 may be adjacent to each other. The fixing member 185 is an example of a "third fixing member" according to the technology of the present disclosure. This configuration makes it possible to supplement insufficiency in ensuring the wide fixing region of the fixing member 51 with the fixing member 185.

Second Embodiment

In the first embodiment, the support table 52 having the attachment surface 53 with an arc surface shape (U-shape) is given as an example. However, the present disclosure is not limited thereto.

Figure 27:
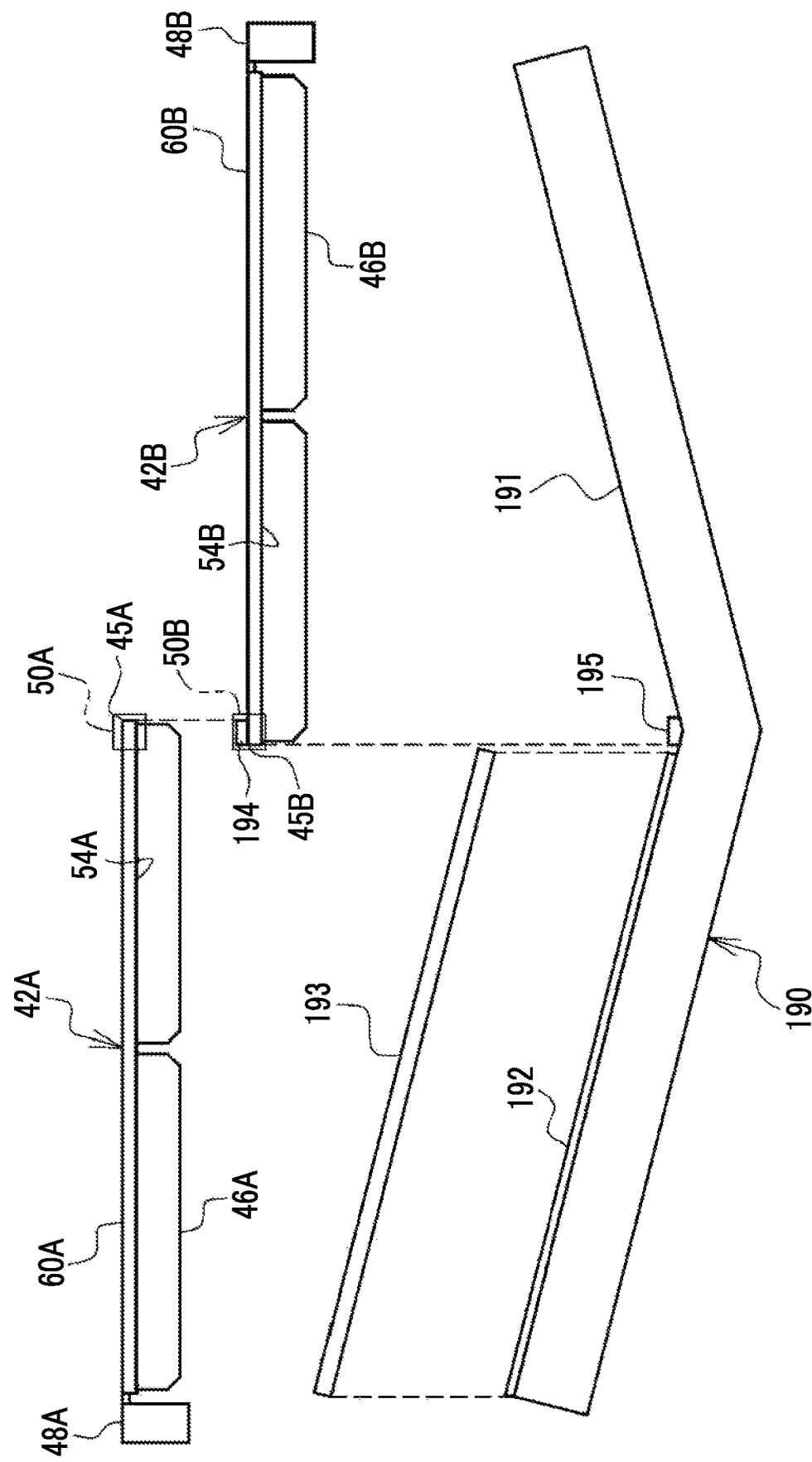
FIG. 27 is an exploded plan view illustrating two sensor panels, a spacer, and a support table in a second embodiment.

For example, as illustrated in FIG. 27, a support table 190 according to a second embodiment has an attachment surface 191 with a V-shape. Here, the "V-shape" is a shape in which most parts including the imaging regions 61A and 61B of the sensor panels 42A and 42B are planar and the end portions 50A and 50B overlapping each other intersect at an angle of less than 180°. Specifically, the "V-shape" means a shape in which both end portions protrude toward one side and both end portions and a central portion are connected by a plane. A spacer 193 is attached to the attachment surface 191 by a fixing member 192. The spacer 193 is a thin plate that has substantially the same size as the sensor panel 42A and has a straight shape following the shape of the attachment surface 191. The spacer 193 has a thickness corresponding to the distance between the sensor panel 42A and the support table 190.

The sensor panels 42A and 42B are fixed by a fixing member 194 in the end portions 50A and 50B. Further, the first surface 54B of the sensor panel 42B is fixed to the attachment surface 191 by a fixing member 195 in the end portion 50B. Therefore, the sensor panel unit 41 has a V-shape following the shape of the attachment surface 191. In addition, the fixing member 194 is an example of the "first fixing member" according to the technology of the present disclosure, and the fixing member 195 is an example of the "second fixing member" according to the technology of the present disclosure.

Figure 28:
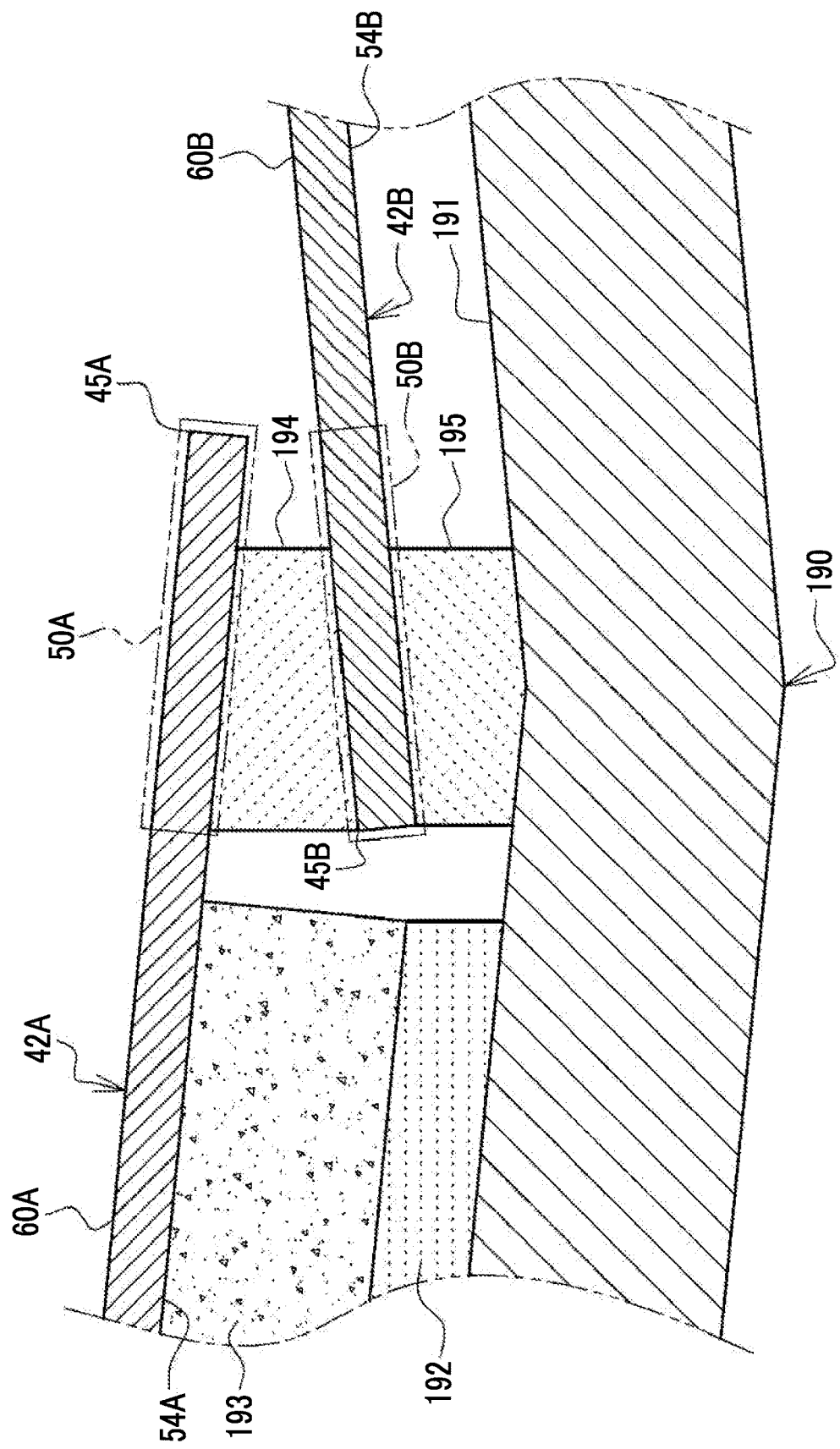
FIG. 28 is a cross-sectional view illustrating the vicinity of an overlap region of end portions of the two sensor panels in the second embodiment.

For example, as illustrated in FIG. 28, the fixing members 194 and 195, particularly, the fixing member 194 has a distorted shape as compared to the simple shape of the fixing members 51 and 59 and the like since the end portion 50A of the sensor panel 42A and the end portion 50B of the sensor panel 42B intersect in a V-shape. Therefore, the fixing members 194 and 195 are made of a material having a higher flexibility in shape than, for example, the fixing members 51 and 59.

Figure 29:
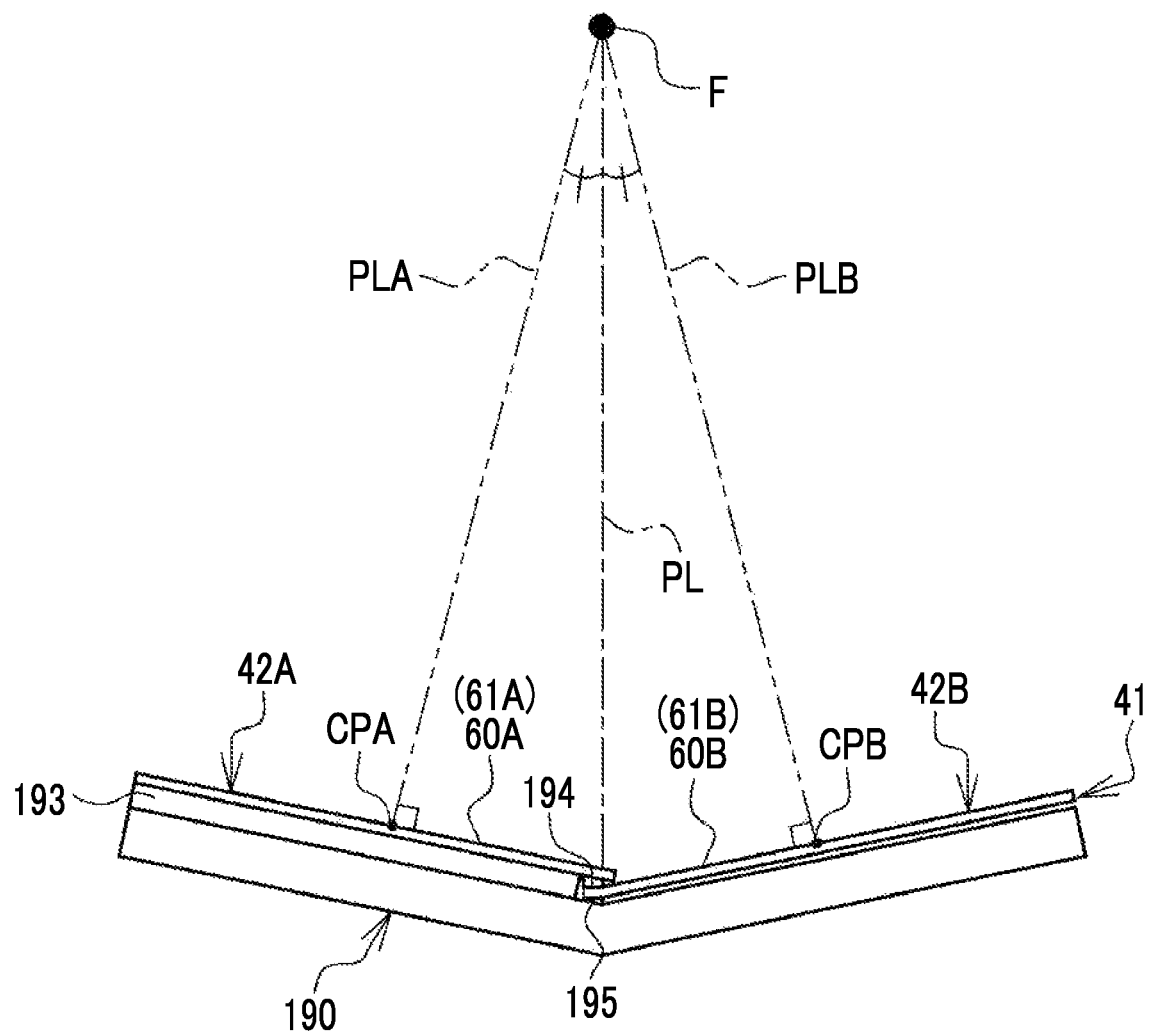
FIG. 29 is a diagram illustrating a positional relationship between a focus of radiation and the sensor panels in the second embodiment.

For example, as illustrated in FIG. 29, in the second embodiment, the perpendicular line PLA drawn from the focus F of the radiation R to the second surface 60A of the sensor panel 42A intersects the center point CPA of the imaging region 61A. Similarly, a perpendicular line PLB drawn from the focus F to the second surface 60B of the sensor panel 42B intersects a center point CPB of the imaging region 61B. The perpendicular lines PLA and PLB have the same length and have the same angle with respect to a perpendicular line PL drawn from the focus F to a center point of the sensor panel unit 41. Therefore, the sensor panels 42A and 42B are substantially mirror-symmetric with respect to the perpendicular line PL.

Even in a case in which the attachment surface 191 has a V-shape and the sensor panel unit 41 has a shape following the shape, the scan field of view sFOV2 can be larger than the scan field of view sFOV1 in a case in which the sensor panel unit 41 is planar. Further, in this case, the substrate 100 of the sensor panel 42 may be made of glass instead of the resin as in the above-mentioned example.

The U-shape is not limited to the exemplified arc surface shape. The shape may be an elliptical arc surface shape or a bowl shape such as a parabolic antenna shape. Further, the frame 18 is not limited to the circular ring and may be a polygonal ring.

The contact members 70 to 72 may be configured so as to transmit the radiation R. For example, the contact members 70 to 72 are formed of a low-density foam. For example, the contact members 70 to 72 are configured to transmit 90% or more of the radiation R emitted at a tube voltage of about 120 kV. With this configuration, the possibility that the contact members 70 to 72 will be reflected in the projection image and thus the tomographic image TI is lower than that in a configuration in which the contact members 70 to 72 are brought into contact with the imaging region 61.

The example in which the rear surface of the substrate 100 is the first surface 54 has been described. However, conversely, the sensor panel 42 may be attached to the support table 52 such that the rear surface of the substrate 100 is the second surface 60.

The CT apparatus 10 is given as an example of the radiography apparatus. However, the present disclosure is not limited thereto. The radiography apparatus may be a simple radiography apparatus that captures the projection images one by one while changing the angle. Further, a radiography apparatus may be used which includes a frame to which two sets of the radiation source 20 and the radiation detector 21 are attached, simultaneously irradiates the front surface and the side surface of the subject S with the radiation R to obtain two projection images, and investigates the anatomical shape of the hip joint and spine of subject S and the connection between the spine and the lower limbs.

The hardware configuration of the computer constituting the control device 12 can be modified in various ways. For example, the control device 12 may be configured by a plurality of computers separated as hardware in order to improve processing capacity and reliability. For example, the functions of the receiving unit 145 and the RW control unit 146 and the functions of the imaging control unit 147, the image processing unit 148, and the display control unit 149 are distributed to two computers. In this case, the two computers constitute the control device 12.

As described above, the hardware configuration of the computer of the control device 12 can be appropriately changed according to required performances, such as processing capacity, safety, and reliability. Further, not only the hardware but also an application program, such as the operation program 140, may be duplicated or may be dispersively stored in a plurality of storages in order to ensure safety and reliability.

In each of the above-described embodiments, for example, the following various processors can be used as the hardware structure of processing units performing various processes, such as the receiving unit 145, the RW control unit 146, the imaging control unit 147, the image processing unit 148, and the display control unit 149. The various processors include, for example, the CPU 132 which is a general-purpose processor executing software (operation program 140) to function as various processing units, a programmable logic device (PLD), such as a field programmable gate array (FPGA), which is a processor whose circuit configuration can be changed after manufacture, and/or a dedicated electric circuit, such as an application specific integrated circuit (ASIC), which is a processor having a dedicated circuit configuration designed to perform a specific process.

One processing unit may be configured by one of the various processors or a combination of two or more processors of the same type or different types (for example, a combination of a plurality of FPGAs and/or a combination of a CPU and an FPGA). Further, a plurality of processing units may be configured by one processor.

A first example of the configuration in which a plurality of processing units are configured by one processor is an aspect in which one processor is configured by a combination of one or more CPUs and software and functions as a plurality of processing units. A representative example of this aspect is a client computer or a server computer. A second example of the configuration is an aspect in which a processor that implements the functions of the entire system including a plurality of processing units using one integrated circuit (IC) chip is used. A representative example of this aspect is a system-on-chip (SoC). As such, various processing units are configured using one or more of the various processors as the hardware structure.

In addition, specifically, an electric circuit (circuitry) obtained by combining circuit elements, such as semiconductor elements, can be used as the hardware structure of the various processors.

In the technology of the present disclosure, the above-described various embodiments and/or various modification examples may be combined with each other. In addition, the present disclosure is not limited to each of the above-described embodiments, and various configurations can be used without departing from the gist of the present disclosure. Furthermore, the technology of the present disclosure extends to a storage medium that non-temporarily stores a program, in addition to the program.

The above descriptions and illustrations are detailed descriptions of portions related to the technology of the present disclosure and are merely examples of the technology of the present disclosure. For example, the above description of the configurations, functions, operations, and effects is the description of examples of the configurations, functions, operations, and effects of portions according to the technology of the present disclosure. Therefore, unnecessary portions may be deleted or new elements may be added or replaced in the above descriptions and illustrations without departing from the gist of the technology of the present disclosure. In addition, in the content of the above description and illustration, the description of, for example, common technical knowledge that does not need to be particularly described to enable the implementation of the technology of the present disclosure is omitted in order to avoid confusion and facilitate the understanding of portions related to the technology of the present disclosure.

In the specification, "A and/or B" is synonymous with "at least one of A or B". That is, "A and/or B" means only A, only B, or a combination of A and B. Further, in the specification, the same concept as "A and/or B" is applied to a case in which the connection of three or more matters is expressed by "and/or".

All of the publications, the patent applications, and the technical standards described in the specification are incorporated by reference herein to the same extent as each individual document, each patent application, and each technical standard are specifically and individually stated to be incorporated by reference.

What is claimed is:

1. A radiation detector comprising:
   an imaging sensor unit which includes at least two imaging sensors of a first imaging sensor and a second imaging sensor that have a rectangular plate shape and include pixels that sense radiation, which has been emitted from a radiation source and transmitted through a subject, or visible light converted from the radiation and generate charge and in which a first end portion of the first imaging sensor and a second end portion of the second imaging sensor are arranged to overlap each other in a thickness direction;
   a support table to which the imaging sensor unit is attached;
   a first fixing member that fixes the first imaging sensor and the second imaging sensor in an overlap region in which the first end portion and the second end portion overlap each other;
   a second fixing member that fixes the imaging sensor unit and the support table in the overlap region and at least partially overlaps the first fixing member in the overlap region in a plan view of the imaging sensor unit in the thickness direction;
   a spacer that is provided between the first imaging sensor and the support table and has a thickness corresponding to a distance between the first imaging sensor and the support table in a case in which the first imaging sensor is disposed closer to an incident side of the radiation than the second imaging sensor in the thickness direction; and
   a third fixing member that fixes the first imaging sensor and the spacer at a position adjacent to the first fixing member.

2. The radiation detector according to claim 1, wherein the first fixing member partially fixes the first imaging sensor and the second imaging sensor, and the second fixing member partially fixes the imaging sensor unit and the support table.

3. The radiation detector according to claim 1, wherein a first imaging region in which the pixels are arranged in the first imaging sensor and a second imaging region in which the pixels are arranged in the second imaging sensor overlap in the overlap region in a plan view of the imaging sensor unit in the thickness direction, and
   in a case in which the first imaging sensor is disposed closer to an incident side of the radiation than the second imaging sensor in the thickness direction, the first fixing member is disposed at a position that does not protrude from an overlap imaging region in which the first imaging region and the second imaging region overlap toward the second imaging region.

4. The radiation detector according to claim 1, wherein the first fixing member has the same width as the overlap region.

5. The radiation detector according to claim 1, wherein the imaging sensor unit includes two imaging sensors of the first imaging sensor and the second imaging sensor.

6. The radiation detector according to claim 1, wherein the support table has an attachment surface that is convex toward an opposite side of the radiation source, and
   the imaging sensor unit is attached to the attachment surface following the convex shape.

7. The radiation detector according to claim 6, wherein the convex shape is a U-shape or a V-shape.

8. The radiation detector according to claim 7, wherein, in a case in which the first imaging sensor is disposed closer to an incident side of the radiation than the second imaging sensor in the thickness direction and the convex shape is the U-shape, a tangent line between the first imaging sensor and the first fixing member is parallel to a tangent line between the second imaging sensor and the second fixing member.

9. The radiation detector according to claim 1, wherein the imaging sensor is a sensor panel in which the pixels including thin film transistors are two-dimensionally arranged.

10. The radiation detector according to claim 9, wherein a substrate of the sensor panel has a thickness that is equal to or less than 100 μm.

11. The radiation detector according to claim 9, wherein the support table is made of metal, and a substrate of the sensor panel is made of a resin.

12. A radiation detector comprising:
    an imaging sensor unit which includes at least two imaging sensors of a first imaging sensor and a second imaging sensor that have a rectangular plate shape and include pixels that sense radiation, which has been emitted from a radiation source and transmitted through a subject, or visible light converted from the radiation and generate charge and in which a first end portion of the first imaging sensor and a second end portion of the second imaging sensor are arranged to overlap each other in a thickness direction;
    a support table to which the imaging sensor unit is attahed;
    a first fixing member that fixes the first imaging sensor and the second imaging sensor in an overlap region in which the first end portion and the second end portion overlap each other; and a second fixing member that fixes the imaging sensor unit and the support table in the overlap region and at least partially overlaps the first fixing member in the overlap region in a plan view of the imaging sensor unit in the thickness direction, wherein the support table has an attachment surface to which a first surface of the imaging sensor is attached, and the radiation detector further comprises a contact member that comes into contact with a second surface of the imaging sensor which is opposite to the first surface.

13. The radiation detector according to claim 12, wherein the contact member biases the imaging sensor to the attachment surface.

14. The radiation detector according to claim 12, wherein the contact member is deformed according to thermal expansion and contraction of the imaging sensor in a direction parallel to the attachment surface.

15. The radiation detector according to claim 12, wherein, in the contact member, a first length along a normal direction to the attachment surface is larger than a second length along a direction parallel to the attachment surface.

16. The radiation detector according to claim 12, wherein the attachment surface has a convex shape toward an opposite side of the radiation source, and a surface of the contact member which comes into contact with the second surface has a shape following the convex shape.

17. The radiation detector according to claim 12, further comprising:
a holding member that holds the contact member while pressing the contact member against the imaging sensor and has a higher rigidity than the contact member.

18. The radiation detector according to claim 12, wherein the second surface has an imaging region in which the pixels are arranged and a non-imaging region which is provided around the imaging region and in which the pixels are not arranged, and
the contact member comes into contact with the non-imaging region.

19. The radiation detector according to claim 12, wherein a circuit board is attached to a first side of the imaging sensor,
the contact member biases the imaging sensor to the attachment surface and includes a first contact member that is disposed on the first side and a second contact member that is disposed on a second side of the imaging sensor which faces the first side and to which the circuit board is not attached, and
the first contact member has a higher biasing force than the second contact member.

20. The radiation detector according to claim 12, wherein a circuit board is attached to the imaging sensor, and a radiation shielding member that shields the radiation to protect the circuit board is attached to the contact member.

21. A radiography apparatus comprising:
the radiation detector according to claim 1; and
the radiation source.

22. A radiography apparatus comprising:
a radiation source;
a radiation detector having:
an imaging sensor unit which includes at least two imaging sensors of a first imaging sensor and a second imaging sensor that have a rectangular plate shape and include pixels that sense radiation, which has been emitted from the radiation source and transmitted through a subject, or visible light converted from the radiation and generate charge and in which a first end portion of the first imaging sensor and a second end portion of the second imaging sensor are arranged to overlap each other in a thickness direction,
a support table to which the imaging sensor unit is attached,
a first fixing member that fixes the first imaging sensor and the second imaging sensor in an overlap region in which the first end portion and the second end portion overlap each other, and
a second fixing member that fixes the imaging sensor unit and the support table in the overlap region and at least partially overlaps the first fixing member in the overlap region in a plan view of the imaging sensor unit in the thickness direction;
an annular frame to which the radiation detector and the radiation source are attached and in which a subject is positioned in a cavity; and
a rotation mechanism that rotates the frame around the subject to capture radiographic images of the subject at different angles,
wherein the support table has an attachment surface that has an arc surface shape following the annular frame, and
the imaging sensor unit is attached to the attachment surface following the arc surface shape.

23. The radiography apparatus according to claim 22, wherein the radiography apparatus is a computed tomography apparatus that obtains a tomographic image of the subject on the basis of the radiographic images captured at different angles.

24. The radiography apparatus according to claim 22, wherein the radiation source emits the radiation having a conical shape.

25. The radiography apparatus according to claim 22, wherein the subject is positioned in the cavity in either a standing posture or a sitting posture.

* * * * *